US008921058B2

(12) United States Patent
Grifantini et al.

(10) Patent No.: US 8,921,058 B2
(45) Date of Patent: Dec. 30, 2014

(54) PROSTATE TUMOR MARKERS AND METHODS OF USE THEREOF

(75) Inventors: Renata Grifantini, Siena (IT); Piero Pileri, Siena (IT); Susanna Campagnoli, Siena (IT); Alberto Grandi, Siena (IT); Matteo Parri, Siena (IT); Andrea Pierleoni, Siena (IT); Renzo Nogarotto, Siena (IT)

(73) Assignee: Externautics SpA, Siena (IT)

( * ) Notice: Subject to any disclaimer, the term of this patent is extended or adjusted under 35 U.S.C. 154(b) by 26 days.

(21) Appl. No.: 13/503,396

(22) PCT Filed: Oct. 26, 2010

(86) PCT No.: PCT/EP2010/066134
§ 371 (c)(1),
(2), (4) Date: Sep. 10, 2012

(87) PCT Pub. No.: WO2011/051271
PCT Pub. Date: May 5, 2011

(65) Prior Publication Data
US 2012/0322074 A1    Dec. 20, 2012

(30) Foreign Application Priority Data
Oct. 26, 2009   (EP) .................................. 09174064

(51) Int. Cl.
G01N 33/574   (2006.01)
C07K 14/47   (2006.01)
C07K 16/30   (2006.01)
A61K 38/00   (2006.01)

(52) U.S. Cl.
CPC ...... *G01N 33/57434* (2013.01); *C07K 16/3069* (2013.01); *A61K 38/00* (2013.01); *G01N 2500/00* (2013.01)
USPC ........................................ 435/7.23; 530/350

(58) Field of Classification Search
None
See application file for complete search history.

(56) References Cited

U.S. PATENT DOCUMENTS

| | | |
|---|---|---|
| 2002/0064818 A1 | 5/2002 | Ni et al. |
| 2002/0137044 A1 | 9/2002 | Tang et al. |
| 2003/0186866 A1 | 10/2003 | Baker et al. |
| 2006/0204503 A1 | 9/2006 | Fitchett et al. |
| 2006/0275794 A1 | 12/2006 | Carrino et al. |
| 2007/0020637 A1* | 1/2007 | Isogai et al. ............ 435/6 |
| 2007/0072178 A1 | 3/2007 | Haferlach et al. |
| 2007/0237770 A1 | 10/2007 | Lai et al. |
| 2007/0298445 A1 | 12/2007 | Boyd et al. |
| 2008/0166340 A1 | 7/2008 | Tureci et al. |

FOREIGN PATENT DOCUMENTS

| | | |
|---|---|---|
| EP | 1440981 | 7/2004 |
| EP | 1696029 | 8/2006 |
| WO | WO 99/15653 | 4/1999 |
| WO | WO 99/32639 | 7/1999 |
| WO | WO 00/53758 | 9/2000 |
| WO | WO 02/24888 | 3/2002 |
| WO | WO 02/074961 | 9/2002 |
| WO | WO 02/086443 | 10/2002 |
| WO | WO 2004/058288 | 7/2004 |
| WO | WO 2004/087874 | 10/2004 |
| WO | WO 2004/094623 | 11/2004 |
| WO | WO 2005/030250 | 4/2005 |
| WO | WO 2007/109376 | 9/2007 |
| WO | WO 2008/004719 | 1/2008 |
| WO | WO 2008/021290 | 2/2008 |
| WO | WO 2009/087978 | 7/2009 |
| WO | WO 2010/024677 | 3/2010 |

OTHER PUBLICATIONS

International Report on Patentability for International Application No. PCT/EP2010/066134, mailed May 1, 2012, 10 pages.
International Search Report and Written Opinion for International Application No. PCT/EP2010/066134, mailed May 16, 2011, 17 pages.
Adachi et al., "The human urinary proteome contains more than 1500 proteins, including a large proportion of membrane proteins," *Genome Biology*, Sep. 2006, 7:R80.
Bjartell et al., "Immunohistochemical Detection of Cysteine-Rich Secretory Protein 3 in Tissue and in Serum From Men With Cancer or Benign Enlargement of the Prostate Gland," *The Prostate*, 2006, 66:591-603.
Bjartell et al., "Association of Cysteine-Rich Secretory Protein 3 and β2—Microseminoprotein with Outcome after Radical Prostatectomy," *Clin Cancer Res*, 2007, 13(14):4130-4138.
Bouis et al., "Effect of CDT6 on Factors of Angiogenic Balance in Tumour Cell Lines," *Anticancer Research*, 2007, 27:2325-2330.
Bromberg et al., "Increased Expression of the E3 Ubiquitin Ligase RNF5 is Associated with Decreased Survival in Breast Cancer," *Cancer Res.*, 2007, 67(17):8172-8179.
Chen et al., "Protein profiles associated with survival in lung adenocarcinoma," *PNAS*, Nov. 2003, 100(23):13537-13542.
Didier et al., "RNF5, a RING Finger Protein that Regulates Cell Motility by Targeting Paxillin Ubiquitination and Altered Localization," *Molecular and Cellular Biology*, Aug. 2003, 23(15):5331-5345.

(Continued)

*Primary Examiner* — Brad Duffy
*Assistant Examiner* — Nelson B Moseley, II
(74) *Attorney, Agent, or Firm* — Fish & Richardson P.C.

(57) ABSTRACT

Newly identified proteins as markers for the detection of prostate tumors, or as targets for their therapeutic treatment, affinity ligands capable of selectively interacting with said markers as well as methods for tumor diagnosis and therapy using the same.

12 Claims, 14 Drawing Sheets

(56) References Cited

OTHER PUBLICATIONS

Garcia-Rudaz et al., "Fxna, a novel gene differentially expressed in the rat ovary at the time of folliculogenesis, is required for normal ovarian histogenesis," *Development*, 2007, 134:945-957.

Ginestier et al., "Distinct and complementary information provided by use of tissue and DNA microarrays in the study of breast tumor markers," *Am. J. Pathol.*, 2002 161: 1223-1233.

Gygi et al., "Correlation between Protein and mRNA abundance in Yeast," *Molecular and Cellular Biology*, Mar. 1999, 19(3):1720-1730.

Huang et al., "Comprehensive Genome and Transcriptome Analysis of the 11q13 Amplicon in Human Oral Cancer and Synteny to the 7F5 Amplicon in Murine Oral Carcinoma," *Genes, Chromosomes & Cancer*, 2006, 45:1058-1069.

Kagara et al., "Zinc and its transporter ZIP10 are involved in invasive behavior of breast cancer cells," *Cancer Sci*, May 2007, 98(5):692-697.

Kasper et al., "Expression levels of the putative zinc transporter LIV-1 are associated with a better outcome of breast cancer patients," *Int. J. Cancer*, 2005, 117:961-973.

Krätzschmar et al., "The human cysteine-rich secretory protein (CRISP) family: Primary structure and tissue distribution of CRISP-1, CRISP-2 and CRISP-3," *Eur. J. Biochem*, 1996, 236:827-836.

Nguyen et al., "Identification of a predictive gene expression signature of cervical lymph node metastasis in oral squamous cell carcinoma," *Cancer Sci*, May 2007, 98(5):741-746.

Nicholas et al., "Shotgun proteomic analysis of human-induced sputum," *Proteomics*, 2006, 6:1390-4401.

Nishizuka et al., "Proteomic profiling of the NCI-60 cancer cell lines using new high-density reverse-phase lysate microarrays," *PNAS*, Nov. 2003, 100(24):14229-14234.

Peek et al., "The Angiopoietin-like Factor Cornea-derived Transcript 6 is a Putative Morphogen for Human Cornea," *J. Biol. Chem.,*, Jan. 2002, 277(1):686-693.

Sladek et al., "A genome-wide association study identifies novel risk loci for type 2 diabetes," *Nature*, Feb. 2007, 445:881-885.

Smith et al., "Genome-wide Association Study of Bipolar Disorder in European American and African American Individuals," *Mol .Psychiatry*, Aug. 2009, 14(8):755-763.

Tyers and Mann, "From genomics to proteomics," *Nature*, Mar. 2003, 422:193-197.

Wan et al., "hOLFML1, a novel secreted glycoprotein, enhances the proliferation of human cancer cell lines in vitro," (2008), *FEBS Letters*, 582: 3185-3192.

Anderson et al., A comparison of selected mRNA and protein abundances in human liver; *Electrophoresis* ,18:533-537 (1997).

Adachi J, et al.; The human urinary proteome contains more than 1500 proteins including a large proportion of membranes proteins; (2006) Genome Biol. ; 7:R80.

Adams G.P. et al.; (2005); Monoclonal antibody therapy cancer. Nat Biotechnol. 23: 1 147-1 157.

Albrecht et al.; Zinc Transporter MRNA Expression in the RWPE-1 Human Prostate Epithelial Cell Line; Biometals; vol. 21, No. 4; Aug. 2008; pp. 405-416.

Aslanidis C, et al.; (1990); Ligation-independent cloning of PCR products (LIC-PCR). Nucleic Acids Res. 18:6069-74.

Ausch C, et al.: (2009) Caspase-cleaved cytokeratin 18 fragment (M30) as marker of postoperative residual tumor load in colon cancer patients, Eur. J. Surg. Oncol., vol. 35, No. 11, 1164-1168.

Chauhan, et al.; Aberrant Expression of MUC4 in Ovarian Carcinoma: Diagnostic Significance Alone and in Combination with MUC1 and MUC16 (CA125); Modern Pathology: An Official Journal of the United States and Canadian Academy of Pathology; Oct. 2006; vol. 19, No. 10; pp. 1386-1394.

Database accession No. ADQ66904; sequence 4065; http://www.ebi.ac.uk/Tools/dbfetch/; retrieved on Dec. 3, 2013, 3 pages.

Database accession No. CQ843230; sequence 1877; http://www.ebi.ac.uk/Tools/dbfetch/; retrieved on Dec. 3, 2013, 2 pages.

Ghaemmaghami et al.; "Global analysis of protein expression in yeast"; Nature, 425: 737-741, 2003.

Huang J, et al.; (2010); Genetic and epigenetic silencing of SCARA5 may contribute to human hepatocellular carcinoma by activating FAK signaling. J Clin Invest. 120:223-41.

International Preliminary Report on Patentability and Written Opinion; PCT/EP2010/066144; May 1, 2012; 8 pp.

International Preliminary Report on Patentability and Written Opinion; PCT/EP2010/066147; May 1, 2012; 10 pages.

International Preliminary Report on Patentability and Written Opinion; PCT/EP2011/056825; Nov. 6, 2012; 8 pp.

International Preliminary Report on Patentability; PCT/EP2010/066146; Y. Cussac; May 1, 2012; 10 pp.

International Preliminary Report on Patentability; PCT/EP2010/066154; A. Wittmann-Regis; May 1, 2012; 8 pp.

International Search Report and Written Opinion; PCT/EP2010/066144; Mar. 4, 2011; 15 pp.

International Search Report and Written Opinion; PCT/EP2010/066146; Mar. 18, 2011; M. Langer; 17 pp.

International Search Report and Written Opinion; PCT/EP2010/066147; Mar. 21, 2011; 17 pages.

International Search Report and Written Opinion; PCT/EP2010/066154; Apr. 11, 2011;M. Langer and T. Vogt; 16 pp.

International Search Report; PCT/EP2011/056825; A. Weijland; Aug. 18, 2011.; 5 pp.

Jiang; "Lipids and Lipoproteins: Identification and Characterization of Murine SCARA5, a Novel Class A Scavenger Receptor That Is Expressed by Populations of Epithelial Cells"; J. Biol. Chem. 2006, 281:11834-11845.

Kallioniemi OP, et al.; (2001) Tissue microarray technology for high-throughput molecular profiling of cancer. Hum Mol Genet. 10:657-62.

Kononen J, et al.; (1998); Tissue microarrays for high-throughput molecular profiling of tumor specimens. Nat Med. 4:844-7.

Li JY, et al.; (2009); SCARA5 is a ferritin receptor mediating non-transferrin iron delivery. Dev Cell. 16:35-46.

Parri et al.; "Angiopoietin-like 7, a novel pro-angiogenetic factor over-expressed in cancer"; Angiogenesis; Jun. 6, 2014; 16 pp.

Studier FW. (2005); Protein production by auto-induction in high density shaking cultures. Protein Expr Purif. 41 :207-34.

Yang, et al.; (2005), Polyethylene Glycol-Mediated Cell Fusion, Springer Protocols, 325 :59-66, DOI—10.1385/1-59745-005-7:59).

Yin, Beatrice et al.; Ovarian Cancer Antigen CA125 is Encoded by the MUC16 Mucin Gene; International Journal of Cancer; Apr. 10, 2002; vol. 98, No. 5; pp. 737-740.

\* cited by examiner

Normal prostate

Prostate cancer

Normal prostate

Prostate cancer

Normal prostate

Prostate cancer

Normal prostate

Prostate cancer ns types of cancers in combination with other chemotherapeutic agents. Similarly, Rituximab (Rituxan), a monoclonal antibody targeting the CD20 receptor was approved for the treatment of certain lymphomas in combination with other drugs. As aforementioned, the identification of novel tumor-associated markers is of paramount importance for the clinical diagnosis and treatment of tumors and for the development of novel drugs and therapeutics. Importantly, the development of novel anti-cancer therapeutic agents is extremely beneficial to patients. In this context, antibody-based therapies targeting tumor markers and preferably administered in association with chemotherapy drugs, could lead to complete tumor remission of the disease.

SEQUENCE LISTING

```
<160> NUMBER OF SEQ ID NOS: 20

<210> SEQ ID NO 1
<211> LENGTH: 236
<212> TYPE: PRT
<213> ORGANISM: Homo sapiens

<400> SEQUENCE: 1

Met Thr Ala Glu Phe Leu Ser Leu Leu Cys Leu Gly Leu Cys Leu Gly
1               5                   10                  15

Tyr Glu Asp Glu Lys Lys Asn Glu Lys Pro Pro Lys Pro Ser Leu His
            20                  25                  30
```

-continued

```
Ala Trp Pro Ser Ser Val Val Glu Ala Glu Ser Asn Val Thr Leu Lys
            35                  40                  45

Cys Gln Ala His Ser Gln Asn Val Thr Phe Val Leu Arg Lys Val Asn
 50                  55                  60

Asp Ser Gly Tyr Lys Gln Glu Gln Ser Ser Ala Glu Asn Glu Ala Glu
 65                  70                  75                  80

Phe Pro Phe Thr Asp Leu Lys Pro Lys Asp Ala Gly Arg Tyr Phe Cys
                    85                  90                  95

Ala Tyr Lys Thr Thr Ala Ser His Glu Trp Ser Glu Ser Glu His
            100                 105                 110

Leu Gln Leu Val Val Thr Asp Lys His Asp Glu Leu Glu Ala Pro Ser
            115                 120                 125

Met Lys Thr Asp Thr Arg Thr Ile Phe Val Ala Ile Phe Ser Cys Ile
130                 135                 140

Ser Ile Leu Leu Leu Phe Leu Ser Val Phe Ile Ile Tyr Arg Cys Ser
145                 150                 155                 160

Gln His Ser Ser Ser Glu Glu Ser Thr Lys Arg Thr Ser His Ser
                    165                 170                 175

Lys Leu Pro Glu Gln Glu Ala Ala Glu Ala Asp Leu Ser Asn Met Glu
            180                 185                 190

Arg Val Ser Leu Ser Thr Ala Asp Pro Gln Gly Val Thr Tyr Ala Glu
            195                 200                 205

Leu Ser Thr Ser Ala Leu Ser Glu Ala Ala Ser Asp Thr Thr Gln Glu
            210                 215                 220

Pro Pro Gly Ser His Glu Tyr Ala Ala Leu Lys Val
225                 230                 235

<210> SEQ ID NO 2
<211> LENGTH: 205
<212> TYPE: PRT
<213> ORGANISM: Homo sapiens

<400> SEQUENCE: 2

Met Thr Ala Glu Phe Leu Ser Leu Leu Cys Leu Gly Leu Cys Leu Gly
 1               5                   10                  15

Tyr Glu Asp Glu Lys Lys Asn Glu Lys Pro Pro Lys Pro Ser Leu His
                    20                  25                  30

Ala Trp Pro Ser Ser Val Val Glu Ala Glu Ser Asn Val Thr Leu Lys
            35                  40                  45

Cys Gln Ala His Ser Gln Asn Val Thr Phe Val Leu Arg Lys Val Asn
 50                  55                  60

Asp Ser Gly Tyr Lys Gln Glu Gln Ser Ser Ala Glu Asn Glu Ala Glu
 65                  70                  75                  80

Phe Pro Phe Thr Asp Leu Lys Pro Lys Asp Ala Gly Arg Tyr Phe Cys
                    85                  90                  95

Ala Tyr Lys Thr Thr Ala Ser His Glu Trp Ser Glu Ser Glu His
            100                 105                 110

Leu Gln Leu Val Val Thr Asp Lys His Asp Glu Leu Glu Ala Pro Ser
            115                 120                 125

Met Lys Thr Gly Ser Ser Glu Glu Ser Thr Lys Arg Thr Ser His
130                 135                 140

Ser Lys Leu Pro Glu Gln Glu Ala Ala Glu Ala Asp Leu Ser Asn Met
145                 150                 155                 160

Glu Arg Val Ser Leu Ser Thr Ala Asp Pro Gln Gly Val Thr Tyr Ala
                    165                 170                 175
```

-continued

Glu Leu Ser Thr Ser Ala Leu Ser Glu Ala Ala Ser Asp Thr Thr Gln
            180                 185                 190

Glu Pro Pro Gly Ser His Glu Tyr Ala Ala Leu Lys Val
            195                 200                 205

<210> SEQ ID NO 3
<211> LENGTH: 1015
<212> TYPE: DNA
<213> ORGANISM: Homo sapiens

<400> SEQUENCE: 3

| | | | | | |
|---|---|---|---|---|---|
| gtgagaagga | aactgcaaga | gtggggcaga | gaaccagagt | gtcagagcaa | aacctcctct | 60 |
| atctgcacat | cctggggacg | aaccgggcag | ccggagagct | gcggccggcc | cagtcccgct | 120 |
| ccgcctttga | agggtaaaac | ccaaggcggg | gccttggttc | tggcagaagg | gacgctatga | 180 |
| ccgcagaatt | cctctcc ctg | ctttgcctcg | ggctgtgtct | gggctacgaa | gatgagaaaa | 240 |
| agaatgagaa | accgcccaag | ccctcc ctcc | acgcctggcc | cagctcggtg | gttgaagccg | 300 |
| agagcaatgt | gaccctgaag | tgtcaggctc | attcccagaa | tgtgacattt | gtgctgcgca | 360 |
| aggtgaacga | ctctgggtac | aagcaggaac | agagctcggc | agaaaacgaa | gctgaattcc | 420 |
| ccttcacgga | cctgaagcct | aaggatgctg | ggaggtactt | ttgtgcctac | aagacaacag | 480 |
| cctcccatga | gtggtcagaa | agcagtgaac | acttgcagct | ggtggtcaca | gataaacacg | 540 |
| atgaacttga | agctccctca | atgaaaacag | acaccagaac | catctttgtc | gccatcttca | 600 |
| gctgcatctc | catccttctc | ctcttcctct | cagtcttcat | catctacaga | tgcagccagc | 660 |
| acagttcatc | atctgaggaa | tccaccaaga | gaaccagcca | ttccaaactt | ccggagcagg | 720 |
| aggctgccga | ggcagattta | tccaatatgg | aaagggtatc | tctctcgacg | gcagaccccc | 780 |
| aaggagtgac | ctatgctgag | ctaagcacca | gcgccctgtc | tgaggcagct | tcagacacca | 840 |
| cccaggagcc | cccaggatct | catgaatatg | cggcactgaa | agtgtagcaa | gaagacagcc | 900 |
| ctggccacta | aggaggggg | gatcgtgctg | gccaaggtta | tcggaaatct | ggagatgcag | 960 |
| atactgtgtt | tccttgctct | tcgtccatat | caataaaatt | aagtttctcg | tctta | 1015 |

<210> SEQ ID NO 4
<211> LENGTH: 922
<212> TYPE: DNA
<213> ORGANISM: Homo sapiens

<400> SEQUENCE: 4

| | | | | | |
|---|---|---|---|---|---|
| gtgagaagga | aactgcaaga | gtggggcaga | gaaccagagt | gtcagagcaa | aacctcctct | 60 |
| atctgcacat | cctggggacg | aaccgggcag | ccggagagct | gcggccggcc | cagtcccgct | 120 |
| ccgcctttga | agggtaaaac | ccaaggcggg | gccttggttc | tggcagaagg | gacgctatga | 180 |
| ccgcagaatt | cctctccctg | ctttgcctcg | ggctgtgtct | gggctacgaa | gatgagaaaa | 240 |
| agaatgagaa | accgcccaag | ccctcccctcc | acgcctggcc | cagctcggtg | gttgaagccg | 300 |
| agagcaatgt | gaccctgaag | tgtcaggctc | attcccagaa | tgtgacattt | gtgctgcgca | 360 |
| aggtgaacga | ctctgggtac | aagcaggaac | agagctcggc | agaaaacgaa | gctgaattcc | 420 |
| ccttcacgga | cctgaagcct | aaggatgctg | ggaggtactt | ttgtgcctac | aagacaacag | 480 |
| cctcccatga | gtggtcagaa | agcagtgaac | acttgcagct | ggtggtcaca | gataaacacg | 540 |
| atgaacttga | agctccctca | atgaaaacag | gttcatcatc | tgaggaatcc | accaagagaa | 600 |
| ccagccattc | caaacttccg | gagcaggagg | ctgccgaggc | agatttatcc | aatatggaaa | 660 |

```
gggtatctct ctcgacggca gacccccaag gagtgaccta tgctgagcta agcaccagcg    720
ccctgtctga ggcagcttca gacaccaccc aggagccccc aggatctcat gaatatgcgg    780
cactgaaagt gtagcaagaa gacagccctg gccactaaag gagggggat cgtgctggcc    840 aaggttatcg gaaatctgga gatgcagata ctgtgtttcc ttgctcttcg tccatatcaa    900
taaaattaag tttctcgtct ta                                              922
```

<210> SEQ ID NO 5
<211> LENGTH: 180
<212> TYPE: PRT
<213> ORGANISM: Homo sapiens
<400> SEQUENCE: 5

```
Met Ala Ala Ala Glu Glu Asp Gly Gly Pro Glu Gly Pro Asn Arg
 1               5                  10                  15

Glu Arg Gly Gly Ala Gly Ala Thr Phe Glu Cys Asn Ile Cys Leu Glu
                20                  25                  30

Thr Ala Arg Glu Ala Val Val Ser Val Cys Gly His Leu Tyr Cys Trp
         35                  40                  45

Pro Cys Leu His Gln Trp Leu Glu Thr Arg Pro Glu Arg Gln Glu Cys
     50                  55                  60

Pro Val Cys Lys Ala Gly Ile Ser Arg Glu Lys Val Val Pro Leu Tyr
 65                  70                  75                  80

Gly Arg Gly Ser Gln Lys Pro Gln Asp Pro Arg Leu Lys Thr Pro Pro
                 85                  90                  95

Arg Pro Gln Gly Gln Arg Pro Ala Pro Glu Ser Arg Gly Gly Phe Gln
            100                 105                 110

Pro Phe Gly Asp Thr Gly Gly Phe His Phe Ser Phe Gly Val Gly Ala
        115                 120                 125

Phe Pro Phe Gly Phe Phe Thr Thr Val Phe Asn Ala His Glu Pro Phe
    130                 135                 140

Arg Arg Gly Thr Gly Val Asp Leu Gly Gln Gly His Pro Ala Ser Ser
145                 150                 155                 160

Trp Gln Asp Ser Leu Phe Leu Phe Leu Ala Ile Phe Phe Phe Phe Trp
                165                 170                 175

Leu Leu Ser Ile
            180
```

<210> SEQ ID NO 6
<211> LENGTH: 1168
<212> TYPE: DNA
<213> ORGANISM: Homo sapiens
<400> SEQUENCE: 6

```
gaattctttg tgactggcag gcattcagac caatagtgat taggaaacct tgaagcctgc    60
ccaacgatcg tgggcaggag gtggtttctg gtttgttggg gcgtgtgtat gtgtatttgg   120
ggggactgaa gggtacgtgg ggcgaaacaa accggccat gcagcagcg gaggaggagg    180 acggggccc cgaagggcca atcgcgagc ggggcgggc gggcgcgacc ttcgaatgta     240
atatatgttt ggagactgct cgggaagctg tggtcagtgt gtgtggccac ctgtactgtt   300
ggccatgtct tcatcagtgg ctggagacac ggccagaacg gcaagagtgt ccagtatgta   360
aagctgggat cagcagagag aaggttgtcc cgctttatgg gcgagggagc cagaagcccc   420
aggatcccag attaaaaact ccaccccgcc cccagggcca gagaccagct ccggagagca   480
gagggggatt ccagccattt ggtgataccg ggggcttcca cttctcattt ggtgttggtg   540
```

-continued

```
cttttcccttt tggcttttc accaccgtct tcaatgccca tgagcctttc cgccggggta    600
caggtgtgga tctgggacag ggtcacccag cctccagctg caggattcc ctcttcctgt     660 ttctcgccat cttcttcttt ttttggctgc tcagtatttg agctatgtct gcttcctgcc    720
cacctccagc cagagaagaa tcagtattga gggtccctgc tgaccttcc gtactcctgg     780 acccccttga cccctctatt tctgttggct aaggccagcc ctggacattg tccaggaagg    840
cctggggagg aggagtgaag tctgtgcata gatgggagag ccttctgctc agaggctcac    900
tcagtaacgt tgtttaattc tctgccctgg ggaaggagga tggattgaga gaatgtcttt    960
ctcctctcct aagtctttgc tttccctgat ttcttgattt gatcttcaaa ggtgggcaaa    1020
gttccctctg actcttcccc cactccccat cttactgatt taatttaatt tttcactccc    1080
cagagtctaa tatggattct gactcttaag tgcttccgcc ccctcactac ctcctttaat    1140
acaaattcaa taaaaaggt gaaatata                                        1168
```

<210> SEQ ID NO 7
<211> LENGTH: 157
<212> TYPE: PRT
<213> ORGANISM: Homo sapiens

<400> SEQUENCE: 7

```
Met Leu Pro Glu Gln Gly Pro Gln Pro Ser Thr Met Pro Leu Trp Cys
1               5                   10                  15

Leu Leu Ala Ala Cys Thr Ser Leu Pro Arg Gln Ala Ala Thr Met Leu
            20                  25                  30

Glu Glu Ala Ala Ser Pro Asn Glu Ala Val His Ala Ser Thr Ser Gly
        35                  40                  45

Ser Gly Ala Leu Thr Asp Gln Thr Phe Thr Asp Leu Ser Ala Ala Glu
    50                  55                  60

Ala Ser Ser Glu Glu Val Pro Asp Phe Met Glu Val Pro His Ser Val
65                  70                  75                  80

His His Lys Ile Asn Cys Phe Phe Tyr Leu Glu Lys Gln Leu Cys Gln
                85                  90                  95

Leu Pro Ser Pro Leu Cys Leu Ser Leu Leu Thr Leu Lys Leu Lys
            100                 105                 110

Thr Thr Val Pro Ala Pro Gly Arg Trp Trp Ser Phe Gln Pro His Lys
        115                 120                 125

Ala Phe Pro Leu Leu Val Gly Thr Pro Gly Ser Trp Gln Ser Thr Ile
    130                 135                 140

Asp Pro Ala Trp Ala Ala Pro Ser Gln Pro Ser Pro Gly
145                 150                 155
```

<210> SEQ ID NO 8
<211> LENGTH: 474
<212> TYPE: DNA
<213> ORGANISM: Homo sapiens

<400> SEQUENCE: 8

```
atgcttccag agcaagggcc ccagccttcc acgatgccgc tctggtgcct cctcgccgcc    60
tgcaccagcc tccaaggca ggcagccacc atgctggagg aagctgcttc tcccaacgag    120
gctgtccacg catcaacatc aggcagtggc gcactcactg atcagacatt tacagacctc    180
tcagctgccg aggcctcctc agaggaggtt cctgacttca tggaggtgcc acactctgtt    240
caccataaaa ttaactgctt tttctactta gaaaacaac tctgccaact gccgtccca     300
```

```
ctgtgtctaa gcagcttgct tactttaaaa ttaaaaacaa cggtcccagc tcctggcagg      360
tggtggagct tccagcctca caaggcattc ccacttctgg tgggcactcc tggaagctgg      420
cagagcacaa tcgatcccgc gtgggcggcc ccctctcagc caagcccagg gtga            474
```

<210> SEQ ID NO 9
<211> LENGTH: 279
<212> TYPE: PRT
<213> ORGANISM: Homo sapiens

<400> SEQUENCE: 9

```
Met Met Leu Met Gln Ala Leu Val Leu Phe Thr Leu Asp Ser Leu Asp
1               5                   10                  15

Met Leu Pro Ala Val Lys Ala Thr Trp Leu Tyr Gly Ile Gln Ile Thr
            20                  25                  30

Ser Leu Leu Leu Val Cys Ile Leu Gln Phe Phe Asn Ser Met Ile Leu
        35                  40                  45

Gly Ser Leu Leu Ile Ser Phe Asn Leu Ser Val Phe Ile Ala Arg Lys
    50                  55                  60

Leu Gln Lys Asn Leu Lys Thr Gly Ser Phe Leu Asn Arg Leu Gly Lys
65                  70                  75                  80

Leu Leu Leu His Leu Phe Met Val Leu Cys Leu Thr Leu Phe Leu Asn
                85                  90                  95

Asn Ile Ile Lys Lys Ile Leu Asn Leu Lys Ser Asp Glu His Ile Phe
            100                 105                 110

Lys Phe Leu Lys Ala Lys Phe Gly Leu Gly Ala Thr Arg Asp Phe Asp
        115                 120                 125

Ala Asn Leu Tyr Leu Cys Glu Glu Ala Phe Gly Leu Leu Pro Phe Asn
    130                 135                 140

Thr Phe Gly Arg Leu Ser Asp Thr Leu Leu Phe Tyr Ala Tyr Ile Phe
145                 150                 155                 160

Val Leu Ser Ile Thr Val Ile Val Ala Phe Val Ala Phe His Asn
                165                 170                 175

Leu Ser Asp Ser Thr Asn Gln Gln Ser Val Gly Lys Met Glu Lys Gly
            180                 185                 190

Thr Val Asp Leu Lys Pro Glu Thr Ala Tyr Asn Leu Ile His Thr Ile
        195                 200                 205

Leu Phe Gly Phe Leu Ala Leu Ser Thr Met Arg Met Lys Tyr Leu Trp
    210                 215                 220

Thr Ser His Met Cys Val Phe Ala Ser Phe Gly Leu Cys Ser Pro Glu
225                 230                 235                 240

Ile Trp Glu Leu Leu Leu Lys Ser Val His Leu Tyr Asn Pro Lys Arg
                245                 250                 255

Ile Cys Ile Met Arg Tyr Ser Val Pro Ile Leu Ile Leu Leu Tyr Leu
            260                 265                 270

Cys Tyr Lys Asn Gln Lys Ser
        275
```

<210> SEQ ID NO 10
<211> LENGTH: 102
<212> TYPE: PRT
<213> ORGANISM: Homo sapiens

<400> SEQUENCE: 10

```
Met Met Ser Ile Arg Gln Arg Arg Glu Ile Arg Ala Thr Glu Val Ser
1               5                   10                  15
```

```
Glu Asp Phe Pro Ala Gln Glu Glu Asn Val Lys Leu Glu Asn Lys Leu
                20                  25                  30

Pro Ser Gly Cys Thr Ser Arg Arg Leu Trp Lys Ile Leu Ser Leu Thr
            35                  40                  45

Ile Gly Gly Thr Ile Ala Leu Cys Ile Gly Leu Leu Thr Ser Val Tyr
 50                  55                  60

Leu Ala Thr Leu His Glu Asn Asp Leu Trp Phe Ser Asn Ile Lys Val
 65                  70                  75                  80

Trp Ser Phe Phe Asp His Cys Ile Ile His Ser Val Gly Ser Pro Val
                85                  90                  95

Val Ser His Val Asp Glu
            100
```

<210> SEQ ID NO 11
<211> LENGTH: 716
<212> TYPE: PRT
<213> ORGANISM: Homo sapiens

<400> SEQUENCE: 11

```
Met Met Ser Ile Arg Gln Arg Glu Ile Arg Ala Thr Glu Val Ser
 1               5                  10                  15

Glu Asp Phe Pro Ala Gln Glu Glu Asn Val Lys Leu Glu Asn Lys Leu
                20                  25                  30

Pro Ser Gly Cys Thr Ser Arg Arg Leu Trp Lys Ile Leu Ser Leu Thr
            35                  40                  45

Ile Gly Gly Thr Ile Ala Leu Cys Ile Gly Leu Leu Thr Ser Val Tyr
 50                  55                  60

Leu Ala Thr Leu His Glu Asn Asp Leu Trp Phe Ser Asn Ile Lys Glu
 65                  70                  75                  80

Val Glu Arg Glu Ile Ser Phe Arg Thr Glu Cys Gly Leu Tyr Tyr Ser
                85                  90                  95

Tyr Tyr Lys Gln Met Leu Gln Ala Pro Thr Leu Val Gln Gly Phe His
            100                 105                 110

Gly Leu Ile Tyr Asp Asn Lys Thr Glu Ser Met Lys Thr Ile Asn Leu
            115                 120                 125

Leu Gln Arg Met Asn Ile Tyr Gln Glu Val Phe Leu Ser Ile Leu Tyr
        130                 135                 140

Arg Val Leu Pro Ile Gln Lys Tyr Leu Glu Pro Val Tyr Phe Tyr Ile
145                 150                 155                 160

Tyr Thr Leu Phe Gly Leu Gln Ala Ile Tyr Val Thr Ala Leu Tyr Ile
                165                 170                 175

Thr Ser Trp Leu Leu Ser Gly Thr Trp Leu Ser Gly Leu Leu Ala Ala
            180                 185                 190

Phe Trp Tyr Val Thr Asn Arg Ile Asp Thr Thr Arg Val Glu Phe Thr
        195                 200                 205

Ile Pro Leu Arg Glu Asn Trp Ala Leu Pro Phe Phe Ala Ile Gln Ile
    210                 215                 220

Ala Ala Ile Thr Tyr Phe Leu Arg Pro Asn Leu Gln Pro Leu Ser Glu
225                 230                 235                 240

Arg Leu Thr Leu Leu Ala Ile Phe Ile Ser Thr Phe Leu Phe Ser Leu
                245                 250                 255

Thr Trp Gln Phe Asn Gln Phe Met Met Leu Met Gln Ala Leu Val Leu
            260                 265                 270

Phe Thr Leu Asp Ser Leu Asp Met Leu Pro Ala Val Lys Ala Thr Trp
        275                 280                 285
```

-continued

```
Leu Tyr Gly Ile Gln Ile Thr Ser Leu Leu Val Cys Ile Leu Gln
    290                 295                 300

Phe Phe Asn Ser Met Ile Leu Gly Ser Leu Leu Ile Ser Phe Asn Leu
305                 310                 315                 320

Ser Val Phe Ile Ala Arg Lys Leu Gln Lys Asn Leu Lys Thr Gly Ser
                325                 330                 335

Phe Leu Asn Arg Leu Gly Lys Leu Leu Leu His Leu Phe Met Val Leu
                340                 345                 350

Cys Leu Thr Leu Phe Leu Asn Asn Ile Ile Lys Lys Ile Leu Asn Leu
            355                 360                 365

Lys Ser Asp Glu His Ile Phe Lys Phe Leu Lys Ala Lys Phe Gly Leu
        370                 375                 380

Gly Ala Thr Arg Asp Phe Asp Ala Asn Leu Tyr Leu Cys Glu Glu Ala
385                 390                 395                 400

Phe Gly Leu Leu Pro Phe Asn Thr Phe Gly Arg Leu Ser Asp Thr Leu
                405                 410                 415

Leu Phe Tyr Ala Tyr Ile Phe Val Leu Ser Ile Thr Val Ile Val Ala
                420                 425                 430

Phe Val Val Ala Phe His Asn Leu Ser Asp Ser Thr Asn Gln Gln Ser
            435                 440                 445

Val Gly Lys Met Glu Lys Gly Thr Val Asp Leu Lys Pro Glu Thr Ala
        450                 455                 460

Tyr Asn Leu Ile His Thr Ile Leu Phe Gly Phe Leu Ala Leu Ser Thr
465                 470                 475                 480

Met Arg Met Lys Tyr Leu Trp Thr Ser His Met Cys Val Phe Ala Ser
                485                 490                 495

Phe Gly Leu Cys Ser Pro Glu Ile Trp Glu Leu Leu Leu Lys Ser Val
            500                 505                 510

His Leu Tyr Asn Pro Lys Arg Ile Cys Ile Met Arg Tyr Ser Val Pro
        515                 520                 525

Ile Leu Ile Leu Leu Tyr Leu Cys Tyr Lys Phe Trp Pro Gly Met Met
        530                 535                 540

Asp Glu Leu Ser Glu Leu Arg Glu Phe Tyr Asp Pro Asp Thr Val Glu
545                 550                 555                 560

Leu Met Asn Trp Ile Asn Ser Asn Thr Pro Arg Lys Ala Val Phe Ala
                565                 570                 575

Gly Ser Met Gln Leu Leu Ala Gly Val Lys Leu Cys Thr Gly Arg Thr
            580                 585                 590

Leu Thr Asn His Pro His Tyr Glu Asp Ser Ser Leu Arg Glu Arg Thr
        595                 600                 605

Arg Ala Val Tyr Gln Ile Tyr Ala Lys Arg Ala Pro Glu Glu Val His
        610                 615                 620

Ala Leu Leu Arg Ser Phe Gly Thr Asp Tyr Val Ile Leu Glu Asp Ser
625                 630                 635                 640

Ile Cys Tyr Glu Arg Arg His Arg Arg Gly Cys Arg Leu Arg Asp Leu
                645                 650                 655

Leu Asp Ile Ala Asn Gly His Met Met Asp Gly Pro Gly Glu Asn Asp
            660                 665                 670

Pro Asp Leu Lys Pro Ala Asp His Pro Arg Phe Cys Glu Glu Ile Lys
        675                 680                 685

Arg Asn Leu Pro Pro Tyr Val Ala Tyr Phe Thr Arg Val Phe Gln Asn
    690                 695                 700
```

Lys Thr Phe His Val Tyr Lys Leu Ser Arg Asn Lys
705                 710                 715

<210> SEQ ID NO 12
<211> LENGTH: 112
<212> TYPE: PRT
<213> ORGANISM: Homo sapiens

<400> SEQUENCE: 12

Met Met Ser Ile Arg Gln Arg Arg Glu Ile Arg Ala Thr Glu Val Ser
1               5                   10                  15

Glu Asp Phe Pro Ala Gln Glu Glu Asn Val Lys Leu Glu Asn Lys Leu
                20                  25                  30

Pro Ser Gly Cys Thr Ser Arg Arg Leu Trp Lys Ile Leu Ser Leu Thr
            35                  40                  45

Ile Gly Gly Thr Pro Phe Ala Leu Asp Phe Leu His Leu Ser Thr Leu
        50                  55                  60

Pro Arg Tyr Met Lys Met Ile Tyr Gly Phe Leu Ile Leu Arg Lys Trp
65                  70                  75                  80

Ser Glu Lys Ser His Ser Glu Gln Ser Val Ala Cys Ile Thr Pro Thr
                85                  90                  95

Thr Ser Arg Cys Cys Arg Leu Gln Pro Ser Cys Lys Val Ile Thr Thr
            100                 105                 110

<210> SEQ ID NO 13
<211> LENGTH: 1841
<212> TYPE: DNA
<213> ORGANISM: Homo sapiens

<400> SEQUENCE: 13
aagtttgcgg agcggcttct gctcgtcggc cgtgcggcga ggcagggcct gggctgcgac      60
cccggcggcc gctcgcggtc ttgggagagc tggggcgcgt gcctgaactt cccggctgcc     120
cctgtccttg gagacctacc tgatgggggac gccaggtgtg caggggcgtg cgcgtagga     180 gtgatttgga gaacaatgca gtaagtctg acatcatgat gtccatccgg caagaagag      240 aaataagagc cacagaagtt tctgaagact ttccagccca agaagaaaat gtgaagttgg     300
aaaataaatt gccatctggt tgtaccagta gaagattatg gaagattttg tcattgacaa     360
ttggtggaac cattgccctt tgcattggac ttcttacatc tgtctacctt gccacgttac     420
atgaaaatga tttatggttt tctaatatta aggaagtgga gcgagaaatc tcattcagaa     480
cagagtgtgg cctgtattac tcctactaca agcagatgct gcaggctcca accctcgtgc     540
aaggttttca tggcctaata tatgataata aaactgaatc tatgaagaca attaacctcc     600
ttcagcgaat gaatatttac caagaggttt tctcagtat tttatataga gttctaccca     660
tacagaaata tttagagcca gtttattttt atatttacac cttatttggg ctccaggcga     720
tctatgtcac agctctctac ataaccagct ggctactcag tggtacatgg ctgtcaggac     780
tgttggcagc tttctggtat gtcacaaata gaatagatac cacaagagtt gagtttacca     840
tcccactgag ggagaactgg gcgctgccat tctttgcaat tcagatagca gcaattacat     900
atttcctgag accaaactta cagcctcttt ctgaaaggct gacacttctt gccattttca     960
tatcaacttt tctctttagt ctgacatggc aatttaatca atttatgatg ctgatgcaag    1020
cattagtgct gttcacactg gactccctgg acatgctgcc agcagtgaag gcgacatggc    1080
tgtatggaat acagataaca agtttactcc tggtctgcat tcttcagttt tttaattcca    1140
tgattcttgg atcactgctt atcagttttta acctttcagt attcattgca agaaaacttc    1200

```
agaaaaatct gaaaactgga agcttcctta ataggcttgg gaaacttttg ttacatttat    1260
ttatggtttt atgtttgaca cttttttctca acaacataat taagaaaatt cttaacctga    1320
agtcagatga acacatattt aaatttctga aggcaaaatt tgggcttgga gcaacaaggg    1380
attttgatgc aaatctctat ctgtgtgaag aagcttttgg cctcctgcct tttaatacat    1440
ttggaaggct ttcagatact ctgctttttt atgcttacat attcgttctg tccatcacag    1500
tgattgtagc attcgttgtt gcctttcata atctcagtga ttctacaaat caacaatccg    1560
tgggtaaaat ggaaaaaggc acagttgacc tgaaaccaga aactgcctac aacttaatac    1620
ataccattct gtttggattc ttggcattga gtacaatgag aatgaagtac ctctggacgt    1680
cacacatgtg tgtgttcgca tcattcggcc tatgtagccc tgaaatatgg gagttacttc    1740
tgaagtcagt ccatctttat aacccaaaga ggatatgtat aatgcgatat tcagtaccga    1800
tattaatact gctgtatcta tgctataaga atcagaaatc t                        1841
```

<210> SEQ ID NO 14
<211> LENGTH: 2206
<212> TYPE: DNA
<213> ORGANISM: Homo sapiens

<400> SEQUENCE: 14

```
cggttctgcc ctccttgtac ccgcggcgcg ctgcggcccg tgcgcggcc ccgttcccgc      60 ctagccccgt cggcctcctt cccctcccgg agccgcgcgt gaggacggct gaggccgcag    120
gagtgatttg gagaacaatg catgtaagtc tgacatcatg atgtccatcc ggcaaagaag    180
agaaataaga gccacagaag tttctgaaga cttttccagcc caagaagaaa atgtgaagtt    240
ggaaaataaa ttgccatctg ttgtaccag tagaagatta tggaagattt tgtcattgac    300
aattggtgga accattgccc tttgcattgg acttcttaca tctgtctacc ttgccacgtt    360
acatgaaaat gatttatggt tttctaatat taaggtatgg agtttctttg accattgtat    420
cattcactca gtgggatctc cagtagtaag ccatgtggat gaatgaccaa ggcaacacag    480
ttttgccata aagaatccaa tctctagaaa ggttggacta tagagtgaaa taacttttgt    540
gtttattatt ttaaaataac atattagaat ctttttttaa attttctttt attatttatt    600 tattttttgag atggagtctc actctgtcac ccaggctgga gtgcggtggc gcaatcttgg    660
ctcactacaa cctctgcctc gcaggttcag gtgattcttc tggcttagcc tcccaagtag    720
ctgggactat aggtgcgtgc caccacaccc agctaatttt tgtattttta ctagagacgg    780
ggtttcagca tattgaccag gctgatctcg aactcctgac cttgtgatct gcctgtctca    840
gcctcccaaa gtgctgggat tacaggcgtg agccactgcg tccagccaga atctttattt    900 ttcatttttaa ttttttgaga tagggtattg ctctgtcacc caggctagaa tgcagtggtg    960
caaacatggg tcactgcagc ctcaacctcc tgggctcaag tgagtatcct gcctaagctt    1020
cctgtgtcac tgggaccccca ggcatgcacc acctcaccaa gctaaatttg atttttttgt    1080
agagacaggg tctcactttg ttgcccatgc tggtctcgaa ctcctgggct caagcgatcc    1140
tactgccctg gtcttccaaa atatgagaat gagccatagc acccagccca gaatttttat    1200
aatcaagtga gttttttctt tttcattaac ttattccatt tatttagcag ttattctaaa    1260
ttagtatttt tcaagttata gattgtgaaa ttagtgcagt aggtcatgag taacatttttt    1320 cttaatgaaa tcaaaaagaa agaatactat cacatctagt agggttgagg attgttttgt    1380 gaaacttttta attttatata tatatatata tgcacaaact gggtcacagt atacaaggta    1440
```

```
cttcctttc  ttttttttct  tgttggctac  aacaggaaaa  aaaaaaaaca  gaaaaggaaa   1500
taaaaaagcc  actgctttaa  atcatggggt  ctaaatgtgg  ctccacagag  ggtcctcagc  1560
atgttcatga  ctatctaata  ctctgtgcaa  gtggttttgc  agggcatagg  gcgatgggga  1620
agccatatgt  ttccagggaa  aggaactgta  attttaatca  gattttcagg  agggttagcc  1680
gggcgtcacg  cctgtaatcc  cagcactttg  ggaggtcgag  gcgggcagat  cacttgaagt  1740
caggagttca  agaccagcct  ggccaacatg  gtggaaccct  atctctacta  aaaatacaaa  1800
aattagccgg  gcatggtgac  acacacctgt  aatctcagct  actcaggagg  ctgaggcaca  1860
agaatcactt  gaactcggga  ggaagaggtt  gcagtgagct  gagatcccac  cactgcactc  1920
cagcctgggc  aacagagcaa  tactctttat  caaaaaaaaa  aagaaaaaag  ttgagggggt  1980
ggtctgtgac  tctttaaaca  cgtttccttg  ttttctttct  ctctctcttt  ttcaacattt  2040
ctagaactcc  tcttggcatt  gttttcagaa  ctcgtatata  acttacatgt  ggaaatttgc  2100
atccaaatat  accttacatt  ttaatctaat  atgtcatgat  ctttaaccta  aactgtggtg  2160
tctaatgact  agttgcttgt  aaaaataaac  aaacaccttc  aaagcc                  2206

<210> SEQ ID NO 15
<211> LENGTH: 4456
<212> TYPE: DNA
<213> ORGANISM: Homo sapiens

<400> SEQUENCE: 15
aagtttgcgg  agcggcttct  gctcgtcggc  cgtgcggcga  ggcagggcct  gggctgcgac    60
cccggcggcc  gctcgcggtc  ttgggagagc  tggggcgcgt  gcctgaactt  cccggctgcc   120
cctgtccttg  gagacctacc  tgatgggac   gccaggtgtg  caggggcgtg  gcgcgtagga   180
gtgatttgga  gaacaatgca  tgtaagtctg  acatcatgat  gtccatccgg  caaagaagag   240
aaataagagc  cacagaagtt  tctgaagact  ttccagccca  agaagaaaat  gtgaagttgg   300
aaaataaatt  gccatctggt  tgtaccagta  aagattatg   gaagattttg  tcattgacaa   360
ttggtggaac  cattgccctt  tgcattggac  ttcttacatc  tgtctacctt  gccacgttac   420
atgaaaatga  tttatggttt  tctaatatta  aggaagtgga  gcgagaaatc  tcattcagaa   480
cagagtgtgg  cctgtattac  tcctactaca  agcagatgct  gcaggctcca  accctcgtgc   540
aaggttttca  tggcctaata  tatgataata  aaactgaatc  tatgaagaca  attaacctcc   600
ttcagcgaat  gaatatttac  caagaggttt  ttctcagtat  tttatataga  gttctaccca   660
tacagaaata  tttagagcca  gtttattttt  atatttacac  cttatttggg  ctccaggcga   720
tctatgtcac  agctctctac  ataaccagct  ggctactcag  tggtacatgg  ctgtcaggac   780
tgttggcagc  tttctggtat  gtcacaaata  gaatagatac  cacaagagtt  gagtttacca   840
tcccactgag  ggagaactgg  gcgctgccat  tctttgcaat  tcagatagca  gcaattacat   900
atttcctgag  accaaactta  cagcctcttt  ctgaaaggct  gacacttctt  gccattttca   960
tatcaacttt  tctctttagt  ctgacatggc  aatttaatca  atttatgatg  ctgatgcaag  1020
cattagtgct  gttcacactg  gactccctgg  acatgctgcc  agcagtgaag  gcgacatggc  1080
tgtatggaat  acagataaca  agttactcc   tggtctgcat  tcttcagttt  tttaattcca  1140
tgattcttgg  atcactgctt  atcagtttta  acctttcagt  attcattgca  agaaaacttc  1200
agaaaaatct  gaaactggaa  gcttccttta  ataggcttgg  gaacttttg   ttacatttat  1260 ttatggtttt  atgtttgaca  cttttctca  acaaataat   taagaaaatt  cttaacctga  1320
agtcagatga  acacatattt  aaatttctga  aggcaaaatt  tgggcttgga  gcaacaaggg  1380
```

```
attttgatgc aaatctctat ctgtgtgaag aagcttttgg cctcctgcct tttaatacat    1440
ttggaaggct ttcagatact ctgcttttt atgcttacat attcgttctg tccatcacag     1500
tgattgtagc attcgttgtt gcctttcata atctcagtga ttctacaaat caacaatccg    1560
tgggtaaaat ggaaaaaggc acagttgacc tgaaaccaga aactgcctac aacttaatac    1620
ataccattct gtttggattc ttggcattga gtacaatgag aatgaagtac ctctggacgt    1680
cacacatgtg tgtgttcgca tcattcggcc tatgtagccc tgaaatatgg gagttacttc    1740
tgaagtcagt ccatctttat aacccaaaga ggatatgtat aatgcgatat tcagtaccga    1800
tattaatact gctgtatcta tgctataagt tctggccagg aatgatggat gaactctccg    1860
agttgagaga attctatgat ccagatacag tggagctgat gaactggatt aactctaaca    1920
ctccaagaaa ggctgtgttt gcgggaagca tgcagttgct ggccggagtc aagctgtgca    1980
cgggaaggac cctaaccaac cacccgcact atgaagacag cagcctgaga gagcggacca    2040
gagcggttta tcagatatat gccaagaggg caccagagga agtgcatgcc ctcctaaggt    2100
ccttcggcac tgactacgta atcctggaag acagcatctg ctacgagcgg aggcaccgcc    2160
ggggctgccg actccgggac ctgctggaca ttgccaacgg ccacatgatg gatggcccag    2220
gagagaatga tcctgatttg aaacctgcag accaccctcg cttctgtgaa gagatcaaaa    2280
gaaacctgcc tccctacgtg gcctacttca ccagagtgtt ccagaacaaa accttccacg    2340
tttacaagct gtccagaaac aagtagcgca gatttctgcc cagtgtctat tttgatacg     2400 gagaaactgc atcatgatga aactcaatag atgacgtttc ctatgtaagt aggtagccca    2460
aaccttcaag ctgtgatatg agtaagttct acagatgttt acacaagtgt tgccatcttt    2520
gaaagcatct tctacaagca gaagtctttt tcgttgtgtg tctatctttc tcattaatgt    2580
tctttagcct aaatgttaac aactttctaa gagtgaccta gaattatgtt gttggagaga    2640
atgatgtgtg ttccatggat acctggatag gcacataaca tgttggaaga tgagcacctg    2700
ctcaggattt gaaatacgtt taattttcag gtgacttaag acagctatga ttgaatcaac    2760
tagagatgat gatcgactta tttaatatga tttcactggt gaagaccaat tggtagcttt    2820
ttaaaaagca ctttagtgtc ctgttttacc ttaaaatgtt ataatatttt ccagttgtca    2880
tgctgtcaac attaacaaaa aaatcatgt taaggctttg tatcaaacat tttgttacac     2940
tctgtctgaa atgtaatgtg gagtacttca gcagtatgtg tcatgtattg tgtgtgtctg    3000
tgtgtgtgca tgtgcacaca tgtgttttaa tgctgggcac agaaaagtgt tacaagttcc    3060
atatcgtaag tccttaaagg ggcagaaata tatgtagcca agtagaattt attacatttt    3120
agtgttatta ttttaaaact tactgatact ctttaacctc tcctgcagta atagttttgc    3180
tttatttctt actcatttca atttattggg tttgcaaaat tttgtaaact ttttgtgttt    3240
ttagcctttg tatttttac agcctagaat cttgcaaagt ctgaatatt tttaaatgtt      3300 ctatcttaac tagttcacta atacagtatt tttagcagac agcattttca gacagcattt    3360
tcataccaag tttgacttgt ggtctccaat cttactggga aggccctggt agtgtaattc    3420
ttttccttat taaaggtaa ccaagtgcct ctaagtcatg cttatttgta aacaacaaag      3480
aagagtatat gtacctgctc aaaatttttt tgataatcgc ttatataatt aatttctaat    3540
gatgaggaca tgtaaaagtt gccagtaaga acatagtatg catttaatta aatcaagatg    3600
gctaatggaa ttaactttct cccctgttct tgccaggtgg aaatgattta agcatttctc    3660
cttgcagttg tattgaagta aattaccata ggcatcaaga tggctgcatc acattttcaa    3720
```

```
atgattttat attcagttgc tacttataaa gcagcattca aaaagtcttt tacactgtca    3780
tgttggacac aagcagactc agcttttatc aaaacttgtt taaataaaaa attgacagta    3840
gctgggttat taaattatgc aactgaaact cctgaattat atcttttctg tatcccttaa    3900
taagattgga gaccactgcc gtttaggata atacaataat aaaacgtttt aatcagtact    3960
aaaactttaa ttaagccaat aatgatgcat gcctgttgta gctgacagca tgggtcagta    4020
catccttcag cgagtgcctt actctaattg aaaccaagca cacgtaaggt acaatatgtt    4080
agactctgtg attttgtttt caaaatcctc tgttatggct atatttaaat ttattttaaa    4140
tattcctgta tgtattcatc taagcatttg ggcatttgga gtcttaatat acaagaaaca    4200
cgtacttaaa tttttatgct tatcaccgca atgatggcaa acagtgattt ttttttttcat    4260 agtttaggtg tcattgttgc cagcaccttt agtgctcagt cttcagtgaa aaatataaag    4320
tgccaaaaaa atcttgcaag acagaatcca tacttaacac tctttccaag acactgtgac    4380
catgtacagt agctatttcc tgatgaccaa atctctcaac gaatcatgtt attaataaat    4440 attttttagca ctcatc                                                   4456

<210> SEQ ID NO 16
<211> LENGTH: 336
<212> TYPE: DNA
<213> ORGANISM: Homo sapiens

<400> SEQUENCE: 16
atgatgtcca tccggcaaag aagagaaata agagccacag aagtttctga agactttcca     60
gcccaagaag aaaatgtgaa gttggaaaat aaattgccat ctggttgtac cagtagaaga    120
ttatggaaga ttttgtcatt gacaattggt ggaaccccct ttgcattgga cttcttacat    180
ctgtctacct tgccacgtta catgaaaatg atttatggtt ttctaatatt aaggaagtgg    240
agcgagaaat ctcattcaga acagagtgtg gcctgtatta ctcctactac aagcagatgc    300
tgcaggctcc aaccctcgtg caaggtaatt acaact                              336

<210> SEQ ID NO 17
<211> LENGTH: 831
<212> TYPE: PRT
<213> ORGANISM: Homo sapiens

<400> SEQUENCE: 17

Met Lys Val His Met His Thr Lys Phe Cys Leu Ile Cys Leu Leu Thr
 1               5                  10                  15

Phe Ile Phe His His Cys Asn His Cys His Glu Glu His Asp His Gly
                20                  25                  30

Pro Glu Ala Leu His Arg Gln His Arg Gly Met Thr Glu Leu Glu Pro
            35                  40                  45

Ser Lys Phe Ser Lys Gln Ala Ala Glu Asn Glu Lys Lys Tyr Tyr Ile
        50                  55                  60

Glu Lys Leu Phe Glu Arg Tyr Gly Glu Asn Gly Arg Leu Ser Phe Phe
 65                  70                  75                  80

Gly Leu Glu Lys Leu Leu Thr Asn Leu Gly Leu Gly Glu Arg Lys Val
                85                  90                  95

Val Glu Ile Asn His Glu Asp Leu Gly His Asp His Val Ser His Leu
               100                 105                 110

Asp Ile Leu Ala Val Gln Glu Gly Lys His Phe His Ser His Asn His
           115                 120                 125

Gln His Ser His Asn His Leu Asn Ser Glu Asn Gln Thr Val Thr Ser
```

```
                130                 135                 140
Val Ser Thr Lys Arg Asn His Lys Cys Asp Pro Glu Lys Glu Thr Val
145                 150                 155                 160

Glu Val Ser Val Lys Ser Asp Lys His Met His Asp His Asn His
                165                 170                 175

Arg Leu Arg His His Arg Leu His His Leu Asp His Asn Asn
                180                 185                 190

Thr His His Phe His Asn Asp Ser Ile Thr Pro Ser Glu Arg Gly Glu
                195                 200                 205

Pro Ser Asn Glu Pro Ser Thr Glu Thr Asn Lys Thr Gln Glu Gln Ser
210                 215                 220

Asp Val Lys Leu Pro Lys Gly Lys Arg Lys Lys Gly Arg Lys Ser
225                 230                 235                 240

Asn Glu Asn Ser Glu Val Ile Thr Pro Gly Phe Pro Asn His Asp
                245                 250                 255

Gln Gly Glu Gln Tyr Glu His Asn Arg Val His Lys Pro Asp Arg Val
                260                 265                 270

His Asn Pro Gly His Ser His Val His Leu Pro Glu Arg Asn Gly His
                275                 280                 285

Asp Pro Gly Arg Gly His Gln Asp Leu Asp Pro Asp Asn Glu Gly Glu
                290                 295                 300

Leu Arg His Thr Arg Lys Arg Glu Ala Pro His Val Lys Asn Asn Ala
305                 310                 315                 320

Ile Ile Ser Leu Arg Lys Asp Leu Asn Glu Asp Asp His His His Glu
                325                 330                 335

Cys Leu Asn Val Thr Gln Leu Leu Lys Tyr Tyr Gly His Gly Ala Asn
                340                 345                 350

Ser Pro Ile Ser Thr Asp Leu Phe Thr Tyr Leu Cys Pro Ala Leu Leu
                355                 360                 365

Tyr Gln Ile Asp Ser Arg Leu Cys Ile Glu His Phe Asp Lys Leu Leu
                370                 375                 380

Val Glu Asp Ile Asn Lys Asp Lys Asn Leu Val Pro Glu Asp Glu Ala
385                 390                 395                 400

Asn Ile Gly Ala Ser Ala Trp Ile Cys Gly Ile Ile Ser Ile Thr Val
                405                 410                 415

Ile Ser Leu Leu Ser Leu Leu Gly Val Ile Leu Val Pro Ile Ile Asn
                420                 425                 430

Gln Gly Cys Phe Lys Phe Leu Leu Thr Phe Leu Val Ala Leu Ala Val
                435                 440                 445

Gly Thr Met Ser Gly Asp Ala Leu Leu His Leu Leu Pro His Ser Gln
450                 455                 460

Gly Gly His Asp His Ser His Gln His Ala His Gly His Gly His Ser
465                 470                 475                 480

His Gly His Glu Ser Asn Lys Phe Leu Glu Glu Tyr Asp Ala Val Leu
                485                 490                 495

Lys Gly Leu Val Ala Leu Gly Gly Ile Tyr Leu Leu Phe Ile Ile Glu
                500                 505                 510

His Cys Ile Arg Met Phe Lys His Tyr Lys Gln Gln Arg Gly Lys Gln
                515                 520                 525

Lys Trp Phe Met Lys Gln Asn Thr Glu Glu Ser Thr Ile Gly Arg Lys
                530                 535                 540

Leu Ser Asp His Lys Leu Asn Asn Thr Pro Asp Ser Asp Trp Leu Gln
545                 550                 555                 560
```

```
Leu Lys Pro Leu Ala Gly Thr Asp Asp Ser Val Val Ser Glu Asp Arg
                565                 570                 575
Leu Asn Glu Thr Glu Leu Thr Asp Leu Glu Gly Gln Gln Glu Ser Pro
            580                 585                 590
Pro Lys Asn Tyr Leu Cys Ile Glu Glu Lys Ile Ile Asp His Ser
        595                 600                 605
His Ser Asp Gly Leu His Thr Ile His Glu His Asp Leu His Ala Ala
    610                 615                 620
Ala His Asn His His Gly Glu Asn Lys Thr Val Leu Arg Lys His Asn
625                 630                 635                 640
His Gln Trp His His Lys His Ser His His Ser His Gly Pro Cys His
                645                 650                 655
Ser Gly Ser Asp Leu Lys Glu Thr Gly Ile Ala Asn Ile Ala Trp Met
            660                 665                 670
Val Ile Met Gly Asp Gly Ile His Asn Phe Ser Asp Gly Leu Ala Ile
        675                 680                 685
Gly Ala Ala Phe Ser Ala Gly Leu Thr Gly Gly Ile Ser Thr Ser Ile
    690                 695                 700
Ala Val Phe Cys His Glu Leu Pro His Glu Leu Gly Asp Phe Ala Val
705                 710                 715                 720
Leu Leu Lys Ala Gly Met Thr Val Lys Gln Ala Ile Val Tyr Asn Leu
                725                 730                 735
Leu Ser Ala Met Met Ala Tyr Ile Gly Met Leu Ile Gly Thr Ala Val
            740                 745                 750
Gly Gln Tyr Ala Asn Asn Ile Thr Leu Trp Ile Phe Ala Val Thr Ala
        755                 760                 765
Gly Met Phe Leu Tyr Val Ala Leu Val Asp Met Leu Pro Glu Met Leu
    770                 775                 780
His Gly Asp Gly Asp Asn Glu Glu His Gly Phe Cys Pro Val Gly Gln
785                 790                 795                 800
Phe Ile Leu Gln Asn Leu Gly Leu Leu Phe Gly Phe Ala Ile Met Leu
                805                 810                 815
Val Ile Ala Leu Tyr Glu Asp Lys Ile Val Phe Asp Ile Gln Phe
            820                 825                 830

<210> SEQ ID NO 18
<211> LENGTH: 831
<212> TYPE: PRT
<213> ORGANISM: Homo sapiens

<400> SEQUENCE: 18

Met Lys Val His Met His Thr Lys Phe Cys Leu Ile Cys Leu Leu Thr
1               5                   10                  15
Phe Ile Phe His His Cys Asn His Cys His Glu Glu His Asp His Gly
            20                  25                  30
Pro Glu Ala Leu His Arg Gln His Arg Gly Met Thr Glu Leu Glu Pro
        35                  40                  45
Ser Lys Phe Ser Lys Gln Ala Ala Glu Asn Glu Lys Lys Tyr Tyr Ile
    50                  55                  60
Glu Lys Leu Phe Glu Arg Tyr Gly Glu Asn Gly Arg Leu Ser Phe Phe
65                  70                  75                  80
Gly Leu Glu Lys Leu Leu Thr Asn Leu Gly Leu Gly Glu Arg Lys Val
                85                  90                  95
Val Glu Ile Asn His Glu Asp Leu Gly His Asp His Val Ser His Leu
```

```
            100                 105                 110
Asp Ile Leu Ala Val Gln Glu Gly Lys His Phe His Ser His Asn His
        115                 120                 125
Gln His Ser His Asn His Leu Asn Ser Glu Asn Gln Thr Val Thr Ser
        130                 135                 140
Val Ser Thr Lys Arg Asn His Lys Cys Asp Pro Glu Lys Glu Thr Val
145                 150                 155                 160
Glu Val Ser Val Lys Ser Asp Asp Lys His Met His Asp His Asn His
                165                 170                 175
Arg Leu Arg His His His Arg Leu His His His Leu Asp His Asn Asn
                180                 185                 190
Thr His His Phe His Asn Asp Ser Ile Thr Pro Ser Glu Arg Gly Glu
        195                 200                 205
Pro Ser Asn Glu Pro Ser Thr Glu Thr Asn Lys Thr Gln Glu Gln Ser
        210                 215                 220
Asp Val Lys Leu Pro Lys Gly Lys Arg Lys Lys Gly Arg Lys Ser
225                 230                 235                 240
Asn Glu Asn Ser Glu Val Ile Thr Pro Gly Phe Pro Pro Asn His Asp
                245                 250                 255
Gln Gly Glu Gln Tyr Glu His Asn Arg Val His Lys Pro Asp Arg Val
                260                 265                 270
His Asn Pro Gly His Ser His Val His Leu Pro Glu Arg Asn Gly His
        275                 280                 285
Asp Pro Gly Arg Gly His Gln Asp Leu Asp Pro Asp Asn Glu Gly Glu
        290                 295                 300
Leu Arg His Thr Arg Lys Arg Glu Ala Pro His Val Lys Asn Asn Ala
305                 310                 315                 320
Ile Ile Ser Leu Arg Lys Asp Leu Asn Glu Asp His His His Glu
                325                 330                 335
Cys Leu Asn Val Thr Gln Leu Leu Lys Tyr Tyr Gly His Gly Ala Asn
                340                 345                 350
Ser Pro Ile Ser Thr Asp Leu Phe Thr Tyr Leu Cys Pro Ala Leu Leu
        355                 360                 365
Tyr Gln Ile Asp Ser Arg Leu Cys Ile Glu His Phe Asp Lys Leu Leu
        370                 375                 380
Val Glu Asp Ile Asn Lys Asp Lys Asn Leu Val Pro Glu Asp Glu Ala
385                 390                 395                 400
Asn Ile Gly Ala Ser Ala Trp Ile Cys Gly Ile Ile Ser Ile Thr Val
                405                 410                 415
Ile Ser Leu Leu Ser Leu Leu Gly Val Ile Leu Val Pro Ile Ile Asn
                420                 425                 430
Gln Gly Cys Phe Lys Phe Leu Leu Thr Phe Leu Val Ala Leu Ala Val
        435                 440                 445
Gly Thr Met Ser Gly Asp Ala Leu Leu His Leu Leu Pro His Ser Gln
        450                 455                 460
Gly Gly His Asp His Ser His Gln His Ala His Gly His Gly His Ser
465                 470                 475                 480
His Gly His Glu Ser Asn Lys Phe Leu Glu Glu Tyr Asp Ala Val Leu
                485                 490                 495
Lys Gly Leu Val Ala Leu Gly Gly Ile Tyr Leu Leu Phe Ile Ile Glu
                500                 505                 510
His Cys Ile Arg Met Phe Lys His Tyr Lys Gln Gln Arg Gly Lys Gln
        515                 520                 525
```

-continued

| | | | | | | | | | | | | |
|---|---|---|---|---|---|---|---|---|---|---|---|---|
| Lys | Trp | Phe | Met | Lys | Gln | Asn | Thr | Glu | Glu | Ser | Thr | Ile | Gly | Arg | Lys |
| | 530 | | | | 535 | | | | 540 | | | | | | |

Lys Trp Phe Met Lys Gln Asn Thr Glu Glu Ser Thr Ile Gly Arg Lys
    530                 535                 540

Leu Ser Asp His Lys Leu Asn Asn Thr Pro Asp Ser Asp Trp Leu Gln
545                 550                 555                 560

Leu Lys Pro Leu Ala Gly Thr Asp Asp Ser Val Val Ser Glu Asp Arg
                565                 570                 575

Leu Asn Glu Thr Glu Leu Thr Asp Leu Glu Gly Gln Gln Glu Ser Pro
            580                 585                 590

Pro Lys Asn Tyr Leu Cys Ile Glu Glu Glu Lys Ile Ile Asp His Ser
        595                 600                 605

His Ser Asp Gly Leu His Thr Ile His Glu His Asp Leu His Ala Ala
    610                 615                 620

Ala His Asn His His Gly Glu Asn Lys Thr Val Leu Arg Lys His Asn
625                 630                 635                 640

His Gln Trp His His Lys His Ser His His Ser His Gly Pro Cys His
                645                 650                 655

Ser Gly Ser Asp Leu Lys Glu Thr Gly Ile Ala Asn Ile Ala Trp Met
            660                 665                 670

Val Ile Met Gly Asp Gly Ile His Asn Phe Ser Asp Gly Leu Ala Ile
        675                 680                 685

Gly Ala Ala Phe Ser Ala Gly Leu Thr Gly Gly Ile Ser Thr Ser Ile
    690                 695                 700

Ala Val Phe Cys His Glu Leu Pro His Glu Leu Gly Asp Phe Ala Val
705                 710                 715                 720

Leu Leu Lys Ala Gly Met Thr Val Lys Gln Ala Ile Val Tyr Asn Leu
                725                 730                 735

Leu Ser Ala Met Met Ala Tyr Ile Gly Met Leu Ile Gly Thr Ala Val
            740                 745                 750

Gly Gln Tyr Ala Asn Asn Ile Thr Leu Trp Ile Phe Ala Val Thr Ala
        755                 760                 765

Gly Met Phe Leu Tyr Val Ala Leu Val Asp Met Leu Pro Glu Met Leu
    770                 775                 780

His Gly Asp Gly Asp Asn Glu Glu His Gly Phe Cys Pro Val Gly Gln
785                 790                 795                 800

Phe Ile Leu Gln Asn Leu Gly Leu Leu Phe Gly Phe Ala Ile Met Leu
                805                 810                 815

Val Ile Ala Leu Tyr Glu Asp Lys Ile Val Phe Asp Ile Gln Phe
            820                 825                 830

<210> SEQ ID NO 19
<211> LENGTH: 5227
<212> TYPE: DNA
<213> ORGANISM: Homo sapiens

<400> SEQUENCE: 19
cacgatttgg tgcagccggg gtttggtacc gagcggagag gagatgcaca cggcactcga    60
gtgtgaggaa aaatagaaat gaaggtacat atgcacacaa aatttttgcct catttgtttg   120 ctgacattta ttttttcatca ttgcaaccat tgccatgaag aacatgacca tggccctgaa   180
gcgcttcaca gacagcatcg tggaatgaca gaattggagc caagcaaatt ttcaaagcaa   240
gctgctgaaa atgaaaaaaa atactatatt gaaaaacttt ttgagcgtta tggtgaaaat   300
ggaagattat cctttttttgg tttggagaaa cttttaacaa acttgggcct tggagagaga   360
aaagtagttg agattaatca tgaggatctt ggccacgatc atgtttctca tttagatatt   420

```
ttggcagttc aagagggaaa gcattttcac tcacataacc accagcattc ccataatcat    480
ttaaattcag aaaatcaaac tgtgaccagt gtatccacaa aaagaaacca taaatgtgat    540
ccagagaaag agacagttga agtgtctgta aaatctgatg ataaacatat gcatgaccat    600
aatcaccgcc tacgtcatca ccatcgtttg catcatcatc ttgatcataa caacactcac    660
cattttcata atgattccat tactcccagt gagcgtgggg agcctagcaa tgaaccttca    720
acagagacca ataaaaccca ggaacaatct gatgttaaac taccgaaagg aaagaggaag    780
aaaaaaggga ggaaaagtaa tgaaaattct gaggttatta caccaggttt tcccccctaac   840
catgatcagg gtgaacagta tgagcataat cgggtccaca aacctgatcg tgtacataac    900
ccaggtcatt ctcatgtaca tcttccagaa cgtaatggtc atgatcctgg tcgtggacac    960
caagatcttg atcctgataa tgaaggtgaa cttcgacata ctagaaagag agaagcacca   1020
catgttaaaa ataatgcaat aatttctttg agaaaagatc taaatgaaga tgaccatcat   1080
catgaatgtt tgaacgtcac tcagttatta aaatactatg gtcatggtgc caactctccc   1140
atctcaactg atttatttac ataccttttgc cctgcattgt tatatcaaat cgacagcaga   1200
ctttgtattg agcattttga caaactttta gttgaagata taaataagga taaaaacctg   1260
gttcctgaag atgaggcaaa tatagggggca tcagcctgga tttgtggtat catttctatc   1320
actgtcatta gcctgctttc cttgctaggc gtgatcttgg ttcctatcat taaccaagga   1380
tgcttcaaat tccttcttac attccttgtt gcattagctg taggaacaat gagtggagac   1440
gcccttcttc atctactgcc ccattctcag ggtggacatg atcacagtca ccaacatgca   1500
catgggcatg gacattctca tggacatgaa tctaacaagt ttttggaaga atatgatgct   1560
gtattgaaag gacttgttgc tctaggaggc atttacttgc tatttatcat tgaacactgc   1620
attagaatgt ttaagcacta caaacaacaa agaggaaaac agaaatggtt tatgaaacag   1680
aacacagaag aatcaactat tggaagaaag ctttcagatc acaagttaaa caatacacca   1740
gattctgact ggcttcaact caagcctctt gccggaactg atgactcggt tgtttctgaa   1800
gatcgactta atgaaactga actgacagat ttagaaggcc aacaagaatc ccctcctaaa   1860
aattaccttt gtatagaaga ggagaaaatc atagaccatt ctcacagtga tggattacat   1920
accattcatg agcatgatct ccatgctgct gcacataacc accacggcga gaacaaaact   1980
gtgctgagga agcataatca ccagtggcac cacaagcatt ctcatcattc ccatggcccc   2040
tgtcattctg gatccgatct gaaagaaaca ggaatagcta atatagcctg atggtgatc    2100
atggggggatg gcatccacaa cttcagtgat gggctcgcaa ttggtgcagc tttcagtgct   2160
ggattgacag gaggaatcag tacttctata gccgtcttct gtcatgaact gccacatgaa   2220
ttaggagatt ttgcagttct tcttaaagca ggcatgactg taaagcaagc aattgtatac   2280
aacctcctct ctgccatgat ggcttacata ggcatgctca taggcacagc tgttggtcag   2340
tatgccaata acatcacact ttggatcttt gcagtcactg caggcatgtt cctctatgta   2400
gccttggtgg atatgcttcc agaaatgttg catggtgatg gtgacaatga agaacatggc   2460
tttttgtcctg tggggcaatt catccttcag aatttaggat tgctctttgg atttgccatt   2520
atgctggtga ttgcccctcta tgaagataaa attgtgtttg acatccagtt ttgacctttc   2580
ccagtaatca ctgttgatta cgagaatgtt accatgcagc tttgcatctg ttccttgtac   2640
tgtatgcaca ttgctcaaag gaaagtcagt ggcttgcact acttacaagt ttcatagatt   2700
tgagcctaac cacaagaggc tggtgcttag tactgttttc cctgcacgta ggggtctttt   2760
```

```
aaaaatataa agcttgtgat aaagagagga gaatatggga ctccatgaac cagtgttgat   2820
atgtttgatt aagacttttc acaaaataat catataaaac actagtctct ttattagtag   2880
aaacttctgt ggctatgcag aaatagagat cgaaccaaaa aaaatcattt aaactttaaa   2940 aatatttaa atggactttg gggagacatt ttttgtgtgt tttaagaatg aattgtagtg    3000
ctctttaatt cagctacata tattcatgtg gtgataggga tcaacttgac acaactttga   3060
aactgcataa agtagacata ggaactagag gaaagctcag gctgcattag agtatgaatt   3120
tagcattggg aaaagccctt attcttgaat ctagagttac tattttttgta tatatttgca  3180 tagtgtttaa acctgcagcc taaactactg aaatttgtga ttgtatgttt gtgtgagctt   3240
cagtttaatg aaagattcat aatggttctt tgtattatta taatacttgg tgttggggtg   3300
ttctttctgt tttgttttt actttaattt tgttttgatt tttttttttt tttttggcg    3360 ggggtaggtg agggtttgga gcatgtggtc tttttaaaaa attgtaaccc tctagaaaat   3420
atcaaagaaa tgaaccagac gtggtttaaa tagttgattt tcctatttta acagtaccaa   3480
ctagttaatt gggaaatgta agttctgaat gttcacattg ctttaccagt ttggcactgg   3540
aaccaagagc acatgtcgtg gctggctaca aggttgtaaa gcagaaaatc gaagtttacc   3600
atgtctgtaa tgtgtacatg aagtgtcaat ttagaacagt tactaggata aactccatta   3660
ttgccatggc tgtcatggta cccaagtgac ttggaagatg catttaaatt actcagctga   3720
aatcacttga tcatcttgtg ccaagatatg ctgttggtgc ctgataggga ttagtctttt   3780
aggtgccctg ttctcctacc ataattgtga atgatttgtg agaagtgcaa gccatgttta   3840
tcctgaattt ttacttaata atttgtatta ctagtcatat gcatgtagct ttctgtttac   3900
atcctatgcc acatggtctt catttatgcc aggtaaactg tatttgaact atgtgcagct   3960
agctttgttt taatctgctt ggcaaccagt gtagctgctg taacaatcta tcttattgtt   4020
caaatatata agagccaaac tcttttccat tccatctaaa atgttttcat ttagtactct   4080
tctttcctcc tactctatga acttcaaaac aaaaacaaaa ctttgagagc agcacatgca   4140
tccaggtatt tatagattat tgccagtgtc ttttctgtat gctataagca agggagctta   4200
ggtgttattt ctttaatta tgcttgaatc tgaaaaatta tttctgactt actccatggc    4260
ctccttataa taagtagaag ttttatatat aattaatttt cagcattggg cactgaatta   4320
ggacagtcct catctcattg cttggcccett caagcaacct agctaaaagg tgctgatatt   4380
ttatttagta ctgccaactt caagtgattt agatatctat ctatctagat ttctgaacca   4440
agatatattt atagttcact tttgggtttt tatacccacg gtaggattct gcattccagc   4500
attaaatctg cttcatttta gaacctttat aaaagcaata gctggaatat actcccagtt   4560
ttaaaataaa tgcctgattg atttaaagca agtaggttat gctgaagtat ataaagaagt   4620
tttatattct ctcaaaaatg gtattatctt tctttatttg ctagattctt acaaatcttt   4680
taagagggct gtaacagttg ctgctagtat tagggttcca catcattcta atgtatagtt   4740
tcaagtctta atagacaatc tgaattccac tacatttctt ttggctccaa cattcctttt   4800
agcttgacca gtctaatta aaatgtgttt gttggaggtc attaacgtta cttgtacaat    4860
gctgtcactg tgtgacatcc atatgaattt tggtatatat caatcaatca atcaatcaca   4920
ttgcattcaa tcaatcagct gtgattgatt gattatgctt agaaatacta tagtaactag   4980
atgcagtgtg aattttttcc attaacaaac aaacaagtca gtggcttaaa tgtgattatg   5040
gtcctgcaag gtgattcttg ctaaaatatc taaacttttg ttttgtttta actgaatcat   5100
tttttaactt aaaaagctgg aaaatatcaa atgctgtttt ttttttttca ttgtcaacag   5160
```

```
tggtgtgtca ttttatgtat gttcctaatg cttatggaac tcctccaaaa taaagttact    5220
caaagag                                                              5227

<210> SEQ ID NO 20
<211> LENGTH: 5432
<212> TYPE: DNA
<213> ORGANISM: Homo sapiens

<400> SEQUENCE: 20
agttgatcac tctgaagctt tttggctaaa gcgtttgggt ttagagcttc cattactcat      60
tcgccttgcc caaggcctca gcaaccgacg ttcgaaagcc aggagaaaag gcgaatgata     120
aagggcgctc cacgcatgcg ttaagaagcc gccccaactc ccccgcggcg ttctttcttg     180
gaacaaaact agcgcggagc cacggaactc cgcagtttgc gtagacttga atttcctatt     240
cctcggacga tccatgtgga atccgaaaaa tagaaatgaa ggtacatatg cacacaaaat     300
tttgcctcat ttgtttgctg acatttattt ttcatcattg caaccattgc catgaagaac     360
atgaccatgg ccctgaagcg cttcacagac agcatcgtgg aatgacagaa ttggagccaa     420
gcaaattttc aaagcaagct gctgaaaatg aaaaaaaata ctatattgaa aaactttttg     480
agcgttatgg tgaaaatgga agattatcct ttttggtttt ggagaaactt ttaacaaact     540
tgggccttgg agagagaaaa gtagttgaga ttaatcatga ggatcttggc cacgatcatg     600
tttctcattt agatatttg gcagttcaag agggaaagca ttttcactca cataaccacc     660
agcattccca taatcattta aattcagaaa atcaaactgt gaccagtgta tccacaaaaa     720
gaaaccataa atgtgatcca gagaagaga cagttgaagt gtctgtaaaa tctgatgata     780
aacatatgca tgaccataat caccgcctac gtcatcacca tcgtttgcat catcatcttg     840
atcataacaa cactcaccat tttcataatg attccattac tcccagtgag cgtggggagc     900
ctagcaatga accttcaaca gagaccaata aaacccagga caatctgat gttaaactac     960 cgaaaggaaa gaggaagaaa aaagggagga aaagtaatga aaattctgag gttattacac    1020
caggttttcc ccctaaccat gatcagggtg aacagtatga gcataatcgg gtccacaaac    1080
ctgatcgtgt ataaacccaa ggtcattctc atgtacatct tccagaacgt aatggtcatg    1140
atcctggtcg tggacaccaa gatcttgatc ctgataatga aggtgaactt cgacatacta    1200
gaaagagaga agcaccacat gttaaaaata atgcaataat ttctttgaga aaagatctaa    1260
atgaagatga ccatcatcat gaatgtttga acgtcactca gttattaaaa tactatggtc    1320
atggtgccaa ctctcccatc tcaactgatt tatttacata cctttgccct gcattgttat    1380
atcaaatcga cagcagactt tgtattgagc attttgacaa actttagtt gaagatataa    1440 ataaggataa aaacctggtt cctgaagatg aggcaaatat aggggcatca gcctggattt    1500
gtggtatcat ttctatcact gtcattagcc tgctttcctt gctaggcgtg atcttggttc    1560
ctatcattaa ccaaggatgc ttcaaattcc ttcttacatt ccttgttgca ttagctgtag    1620
gaacaatgag tggagacgcc cttcttcatc tactgcccca ttctcagggt ggacatgatc    1680
acagtcacca acatgcacat gggcatggac attctcatgg acatgaatct aacaagtttt    1740
tggaagaata tgatgctgta ttgaaggac ttgttgctct aggaggcatt tacttgctat    1800
ttatcattga acactgcatt agaatgttta agcactacaa acaacaaaga ggaaaacaga    1860 aatggttat gaaacagaac acagaagaat caactattgg aagaaagctt tcagatcaca    1920
agttaaacaa tacaccagat tctgactggc ttcaactcaa gcctcttgcc ggaactgatg    1980
```

```
actcggttgt ttctgaagat cgacttaatg aaactgaact gacagattta gaaggccaac    2040
aagaatcccc tcctaaaaat tacctttgta tagaagagga gaaaatcata gaccattctc    2100
acagtgatgg attacatacc attcatgagc atgatctcca tgctgctgca cataaccacc    2160
acggcgagaa caaaactgtg ctgaggaagc ataatcacca gtggcaccac aagcattctc    2220
atcattccca tggcccctgt cattctggat ccgatctgaa agaaacagga atagctaata    2280
tagcctggat ggtgatcatg ggggatggca tccacaactt cagtgatggg ctcgcaattg    2340
gtgcagcttt cagtgctgga ttgacaggag gaatcagtac ttctatagcc gtcttctgtc    2400
atgaactgcc acatgaatta ggagattttg cagttcttct taaagcaggc atgactgtaa    2460
agcaagcaat tgtatacaac ctcctctctg ccatgatggc ttacataggc atgctcatag    2520
gcacagctgt tggtcagtat gccaataaca tcacactttg gatctttgca gtcactgcag    2580
gcatgttcct ctatgtagcc ttggtggata tgcttccaga aatgttgcat ggtgatggtg    2640
acaatgaaga acatggcttt tgtcctgtgg ggcaattcat ccttcagaat ttaggattgc    2700
tctttggatt tgccattatg ctggtgattg ccctctatga agataaaatt gtgtttgaca    2760
tccagttttg acctttccca gtaatcactg ttgattacga gaatgttacc atgcagcttt    2820
gcatctgttc cttgtactgt atgcacattg ctcaaaggaa agtcagtggc ttgcactact    2880
tacaagtttc atagatttga gcctaaccac aagaggctgg tgcttagtac tgttttccct    2940
gcacgtaggg gtcttttaaa aatataaagc ttgtgataaa gagaggagaa tatgggactc    3000
catgaaccag tgttgatatg tttgattaag acttttcaca aaataatcat ataaaacact    3060
agtctcttta ttagtagaaa cttctgtggc tatgcagaaa tagagatcga accaaaaaaa    3120
atcatttaaa ctttaaaaat attttaaatg gactttgggg agacattttt tgtgtgtttt    3180
aagaatgaat tgtagtgctc tttaattcag ctacatatat tcatgtggtg atagggatca    3240
acttgacaca actttgaaac tgcataaagt agacatagga actagaggaa agctcaggct    3300
gcattagagt atgaatttag cattgggaaa agcccttatt cttgaatcta gagttactat    3360
ttttgtatat atttgcatag tgtttaaacc tgcagcctaa actactgaaa tttgtgattg    3420
tatgtttgtg tgagcttcag tttaatgaaa gattcataat ggttctttgt attattataa    3480
tacttggtgt tggggtgttc tttctgtttt gttttttact ttaattttgt tttgattttt    3540
tttttttttt tttggcgggg gtaggtgagg gtttggagca tgtggtcttt ttaaaaaatt    3600
gtaaccctct agaaaatatc aaagaaatga accagacgtg gtttaaatag ttgattttcc    3660
tattttaaca gtaccaacta gttaattggg aaatgtaagt tctgaatgtt cacattgctt    3720
taccagtttg gcactggaac caagagcaca tgtcgtggct ggctacaagg ttgtaaagca    3780
gaaaatcgaa gttaccatgt ctgtaatgt gtacatgaag tgtcaattta gaacagttac    3840
taggataaac tccattattg ccatggctgt catggtaccc aagtgacttg gaagatgcat    3900
ttaaattact cagctgaaat cacttgatca tcttgtgcca agatatgctg ttggtgcctg    3960
atagggatta gtctttagg tgccctgttc tcctaccata attgtgaatg atttgtgaga    4020
agtgcaagcc atgtttatcc tgaattttta cttaataatt tgtattacta gtcatatgca    4080
tgtagctttc tgtttacatc ctatgccaca tggtcttcat ttatgccagg taaactgtat    4140
ttgaactatg tgcagctagc tttgttttaa tctgcttggc aaccagtgta gctgctgtaa    4200
caatctatct tattgttcaa atatataaga gccaaactct tttccattcc atctaaaatg    4260
ttttcattta gtactcttct ttcctcctac tctatgaact tcaaaacaaa aacaaaactt    4320
tgagagcagc acatgcatcc aggtatttat agattattgc cagtgtcttt tctgtatgct    4380
```

```
ataagcaagg gagcttaggt gttatttctt taatttatgc ttgaatctga aaaattattt    4440
ctgacttact ccatggcctc cttataataa gtagaagttt tatatataat taattttcag    4500
cattgggcac tgaattagga cagtcctcat ctcattgctt ggcccttcaa gcaacctagc    4560
taaaaggtgc tgatatttta tttagtactg ccaacttcaa gtgatttaga tatctatcta    4620
tctagatttc tgaaccaaga tatatttata gttcactttt gggtttttat acccacggta    4680
ggattctgca ttccagcatt aaatctgctt cattttagaa cctttataaa agcaatagct    4740
ggaatatact cccagtttta aataaatgc ctgattgatt taaagcaagt aggttatgct     4800
gaagtatata aagaagtttt atattctctc aaaaatggta ttatctttct ttatttgcta    4860
gattcttaca aatcttttaa gagggctgta acagttgctg ctagtattag ggttccacat    4920
cattctaatg tatagtttca agtcttaata gacaatctga attccactac atttcttttg    4980
gctccaacat tccttttagc ttgaccagtc taatttaaaa tgtgtttgtt ggaggtcatt    5040
aacgttactt gtacaatgct gtcactgtgt gacatccata tgaattttgg tatatatcaa    5100
tcaatcaatc aatcacattg cattcaatca atcagctgtg attgattgat tatgcttaga    5160
aatactatag taactagatg cagtgtgaat tttttccatt aacaaacaaa caagtcagtg    5220
gcttaaatgt gattatggtc ctgcaaggtg attcttgcta aaatatctaa acttttgttt    5280
tgttttaact gaatcatttt ttaacttaaa aagctggaaa atatcaaatg ctgttttttt    5340
tttttcattg tcaacagtgg tgtgtcattt tatgtatgtt cctaatgctt atggaactcc    5400
tccaaaataa agttactcaa agagagcaaa ta                                  5432
```

PROSTATE TUMOR MARKERS AND METHODS OF USE THEREOF

The present invention relates to newly identified proteins as markers for the detection of prostate tumors, or as targets for their treatment. Also provided are affinity ligands capable of selectively interacting with the newly identified markers as well as methods for tumor diagnosis and therapy using the same.

BACKGROUND OF THE INVENTION

Tumor Markers (or Biomarkers)

Tumor markers are substances that can be produced by tumor cells or by other cells of the body in response to cancer. In particular, a protein biomarker is either a single protein or a panel of different proteins, that could be used to unambiguously distinguish a disease state. Ideally, a biomarker would have both a high specificity and sensitivity, being represented in a significant percentage of the cases of given disease and not in healthy state.

Biomarkers can be identified in different biological samples, like tissue biopsies or preferably biological fluids (saliva, urine, blood-derivatives and other body fluids), whose collection does not necessitate invasive treatments. Tumor marker levels may be categorized in three major classes on the basis of their clinical use. Diagnostic markers can be used in the detection and diagnosis of cancer. Prognostics markers are indicative of specific outcomes of the disease and can be used to define predictive models that allow the clinicians to predict the likely prognosis of the disease at time of diagnosis. Moreover, prognosis markers are helpful to monitor the patient response to a drug therapy and facilitate a more personalized patient management. A decrease or return to a normal level may indicate that the cancer is responding to therapy, whereas an increase may indicate that the cancer is not responding. After treatment has ended, tumor marker levels may be used to check for recurrence of the tumor. Finally, therapeutic markers can be used to develop tumor-specific drugs or affinity ligand (i.e. antibodies) for a prophylactic intervention.

Currently, although an abnormal tumor marker level may suggest cancer, this alone is usually not enough to accurately diagnose cancer and their measurement in body fluids is frequently combined with other tests, such as a biopsy and radioscopic examination. Frequently, tumor marker levels are not altered in all of people with a certain cancer disease, especially if the cancer is at early stage. Some tumor marker levels can also be altered in patients with noncancerous conditions. Most biomarkers commonly used in clinical practice do not reach a sufficiently high level of specificity and sensitivity to unambiguously distinguish a tumor from a normal state.

To date the number of markers that are expressed abnormally is limited to certain types/subtypes of cancer, some of which are also found in other diseases, www.cancer.gov/cancertopics/factsheet).

For instance, the human epidermal growth factor receptor (HER2) is a marker protein overproduced in about 20% of breast cancers, whose expression is typically associated with a more aggressive and recurrent tumors of this class.

Routine Screening Test for Tumor Diagnosis

Screening tests are a way of detecting cancer early, before there are any symptoms. For a screening test to be helpful, it should have high sensitivity and specificity. Sensitivity refers to the test's ability to identify people who have the disease. Specificity refers to the test's ability to identify people who do not have the disease. Different molecular biology approaches such as analysis of DNA sequencing, small nucleotide polymorphyms, in situ hybridization and whole transcriptional profile analysis have done remarkable progresses to discriminate a tumor state from a normal state and are accelerating the knowledge process in the tumor field. However so far different reasons are delaying their use in the common clinical practice, including the higher analysis complexity and their expensiveness. Other diagnosis tools whose application is increasing in clinics include in situ hybridization and gene sequencing.

Currently, Immuno-HistoChemistry (IHC), a technique that allows the detection of proteins expressed in tissues and cells using specific antibodies, is the most commonly used method for the clinical diagnosis of tumor samples. This technique enables the analysis of cell morphology and the classification of tissue samples on the basis of their immunoreactivity. However, at present, IHC can be used in clinical practice to detect cancerous cells of tumor types for which protein markers and specific antibodies are available. In this context, the identification of a large panel of markers for the most frequent cancer classes would have a great impact in the clinical diagnosis of the disease.

Anti-Cancer Therapies

In the last decades, an overwhelming number of studies remarkably contributed to the comprehension of the molecular mechanisms leading to cancer. However, this scientific progress in the molecular oncology field has not been paralleled by a comparable progress in cancer diagnosis and therapy. Surgery and/or radiotherapy are the still the main modality of local treatment of cancer in the majority of patients. However, these treatments are effective only at initial phases of the disease and in particular for solid tumors of epithelial origin, as is the case of colon, lung, breast, prostate and others, while they are not effective for distant recurrence of the disease. In some tumor classes, chemotherapy treatments have been developed, which generally relies on drugs, hormones and antibodies, targeting specific biological processes used by cancers to grow and spread. However, so far many cancer therapies had limited efficacy due to severity of side effects and overall toxicity. Indeed, a major effort in cancer therapy is the development of treatments able to target specifically tumor cells causing limited damages to surrounding normal cells thereby decreasing adverse side effects. Recent developments in cancer therapy in this direction are encouraging, indicating that in some cases a cancer specific therapy is feasible. In particular, the development and commercialization of humanized monoclonal antibodies that recognize specifically tumor-associated markers and promote the elimination of cancer is one of the most promising solutions that appears to be an extremely favorable market opportunity for pharmaceutical companies. However, at present the number of therapeutic antibodies available on the market or under clinical studies is very limited and restricted to specific cancer classes. So far licensed monoclonal antibodies currently used in clinics for the therapy of specific tumor classes, show only a partial efficacy and are frequently associated with chemotherapies to increase their therapeutic effect.

Administration of Trastuzumab (Herceptin), a commercial monoclonal antibody targeting HER2, a protein overproduced in about 20% of breast cancers, in conjunction with Taxol adjuvant chemotherapy induces tumor remission in about 42% of the cases. Bevacizumab (Avastin) and Cetuximab (Erbitux) are two monoclonal antibodies recently licensed for use in humans, targeting the endothelial and epithelial growth factors respectively that, combined with adjuvant chemotherapy, proved to be effective against different tumor diseases. Bevacizumab proved to be effective in prolonging the life of patients with metastatic colorectal, breast and lung cancers. Cetuximab demostrated efficacy in patients with tumor types refractory to standard chemotherapeutic treatments (Adams G. P. and Weiner L. M. (2005) Monoclonal antibody therapy cancer. *Nat. Biotechnol.* 23:1147-57).

In summary, available screening tests for tumor diagnosis are uncomfortable or invasive and this sometimes limits their applications. Moreover tumor markers available today have a limited utility in clinics due to either their incapability to detect all tumor subtypes of the defined cancers types and/or to distinguish unambiguously tumor vs. normal tissues. Similarly, licensed monoclonal antibodies combined with standard chemotherapies are not effective against the majority of cases. Therefore, there is a great demand for new tools to advance the diagnosis and treatment of cancer.

Experimental Approaches Commonly Used to Identify Tumor Markers

Most popular approaches used to discover new tumor markers are based on genome-wide transcription profile or total protein content analyses of tumor. These studies usually lead to the identification of groups of mRNAs and proteins which are differentially expressed in tumors. Validation experiments then follow to eventually single out, among the hundreds of RNAs/proteins identified, the very few that have the potential to become useful markers. Although often successful, these approaches have several limitations and often, do not provide firm indications on the association of protein markers with tumor. A first limitation is that, since frequently mRNA levels not always correlate with corresponding protein abundance (approx. 50% correlation), studies based on transcription profile do not provide solid information regarding the expression of protein markers in tumor. (1, 2, 3, 4).

A second limitation is that neither transcription profiles nor analysis of total protein content discriminate post-translation modifications, which often occur during oncogenesis. These modifications, including phosphorylations, acetylations, and glycosylations, or protein cleavages influence significantly protein stability, localization, interactions, and functions (5).

As a consequence, large scale studies generally result in long lists of differentially expressed genes that would require complex experimental paths in order to validate the potential markers. However, large scale genomic/proteomic studies reporting novel tumor markers frequently lack of confirmation data on the reported potential novel markers and thus do not provide solid demonstration on the association of the described protein markers with tumor.

The approach that we used to identify the protein markers included in the present invention is based on an innovative immuno-proteomic technology. In essence, a library of recombinant human proteins has been produced from *E. coli* and is being used to generate polyclonal antibodies against each of the recombinant proteins.

The screening of the antibodies library on Tissue microarrays (TMAs) carrying clinical samples from different patients affected by the tumor under investigation lead to the identification of specific tumor marker proteins. Therefore, by screening TMAs with the antibody library, the tumor markers are visualized by immuno-histochemistry, the classical technology applied in all clinical pathology laboratories. Since TMAs also include healthy tissues, the specificity of the antibodies for the tumors can be immediately appreciated and information on the relative level of expression and cellular localization of the markers can be obtained. In our approach the markers are subjected to a validation process consisting in a molecular and cellular characterization.

Altogether, the detection the marker proteins disclosed in the present invention selectively in tumor samples and the subsequent validation experiments lead to an unambiguous confirmation of the marker identity and confirm its association with defined tumor classes. Moreover this process provides an indication of the possible use of the proteins as tools for diagnostic or therapeutic intervention. For instance, markers showing a surface cellular localization could be both diagnostic and therapeutic markers against which both chemical and antibody therapies can be developed. Differently, markers showing a cytoplasmic expression could be more likely considered for the development of tumor diagnostic tests and chemotherapy/small molecules treatments.

SUMMARY OF THE INVENTION

The present invention provides new means for the detection and treatment of prostate tumors, based on the identification of protein markers specific for these tumor types, namely:

i) Dpy-19-like 3 (DPY19L3);
ii) V-set and transmembrane domain containing 1 (VSTM1);
iii) Ring Finger protein 5 (RNF5);
iv) Uncharacterized protein UNQ6126/PRO20091 (UNQ6126);
v) Solute carrier family 39 (zinc transporter), member 10 (SLC39A10).

In one embodiment, the invention provides the use of DPY19L3, VSTM1, RNF5, UNQ6126, SLC39A10, as markers or targets for prostate tumor.

The invention also provides a method for the diagnosis of these cancer types, comprising a step of detecting the above-identified markers in a biological sample, e.g. in a tissue sample of a subject suspected of having or at risk of developing malignancies or susceptible to cancer recurrences.

In addition, the tumor markers identify novel targets for affinity ligands which can be used for therapeutic applications. Also provided are affinity ligands, particularly antibodies, capable of selectively interacting with the newly identified protein markers.

DETAILED DISCLOSURE OF THE INVENTION

The present invention is based on the surprising finding of antibodies that are able to specifically stain prostate tumor tissues from patients, while negative or very poor staining is observed in normal prostate tissues from the same patients. These antibodies have been found to specifically bind to proteins for which no previous association with tumor has been reported. Hence, in a first aspect, the invention provides a prostate tumor marker which is selected from the group consisting of:

i) VSTM1, in one of its variant isoforms SEQ ID NO:1, SEQ ID NO:2, or a different isoform having sequence identity of at least 80%, preferably at least 90%, more preferably at least 95% to SEQ ID NO:1 or SEQ ID NO:2, or a nucleic acid molecule containing a sequence coding for a VSTM1 protein, said encoding sequence being preferably selected from SEQ ID NO:3 and SEQ ID NO:4;

ii) RNF5, SEQ ID NO:5, or a different isoform having sequence identity of at least 80%, preferably at least 90%, more preferably at least 95% to SEQ ID NO:5, or a nucleic acid molecule containing a sequence coding for a RNF5 protein, said encoding sequence being preferably SEQ ID NO: 6;

iii) UNQ6126, SEQ ID NO:7, or a different isoform having sequence identity of at least 80%, preferably at least 90%, more preferably at least 95% to SEQ ID NO:7, or a nucleic acid molecule containing a sequence coding for a UNQ6126 protein, said encoding sequence being preferably SEQ ID NO: 8;

iv) DPY19L3, in one of its variant isoforms SEQ ID NO:9, SEQ ID NO:10, SEQ ID NO:11, SEQ ID NO:12, or a different isoform having sequence identity of at least 80%, preferably at least 90%, more preferably at least 95% to any of SEQ ID NO:9, SEQ ID NO:10, SEQ ID NO:11 or SEQ ID NO:12, or a nucleic acid molecule containing a sequence coding for a DPY19L3 protein, said encoding sequence being preferably selected from SEQ ID NO:13, SEQ ID NO:14, SEQ ID NO:15 and SEQ ID NO:16;

v) SLC39A10, in one of its variant isoforms SEQ ID NO:17, SEQ ID NO:18 or a different isoform having sequence identity of at least 80%, preferably at least 90%, more preferably at least 95% to SEQ ID NO:17 or SEQ ID NO:18, or a nucleic acid molecule containing a sequence coding for a SLC39A10 protein, said encoding sequence being preferably selected from SEQ ID NO:19 and SEQ ID NO:20.

As used herein, "Percent (%) amino acid sequence identity" with respect to the marker protein sequences identified herein indicates the percentage of amino acid residues in a full-length protein variant or isoform according to the invention, or in a portion thereof, that are identical with the amino acid residues in the specific marker sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Identity between nucleotide sequences is preferably determined by the Smith-Waterman homology search algorithm as implemented in the MPSRCH program (Oxford Molecular), using an affine gap search with parameters gap open penalty=12 and gap extension penalty=1.

V-set and transmembrane domain containing 1 (VSTM1; Gene ID: ENSG00000189068; Transcript ID: ENST00000338372, ENST00000376626; Protein ID: ENSP00000343366, ENSP00000365813); is an uncharacterized protein without previous known association with tumor and is preferably used as a marker for prostate tumor, and in general for cancers of this type. As described below, an antibody generated towards VSTM1 protein shows a selective immunoreactivity in histological preparation of prostate cancer tissues which indicates the presence of this protein in these cancer samples. Moreover the protein was detected on the surface of tumor cell lines by the specific antibody, suggesting that it can be exploited as target for affinity ligands with therapeutic activity.

Ring finger protein 5 (RNF5; synonyms: E3 ubiquitin-protein ligase RNF5, HsRma1, Protein G16; Gene ID: ENSG00000183574; Transcript ID ENST00000383289; Protein ID: ENSP00000372776) The protein encoded by this gene contains a RING finger, which is a motif known to be involved in protein-protein interactions. This protein is a membrane-bound ubiquitin ligase. Silencing of RNF5 gene suggested that it can regulate cell motility by targeting paxillin ubiquitination and altering the distribution and localization of paxillin in cytoplasm and cell focal adhesions (6). RNF5 expression has also been reported in some tumor types, but most studies are limited to the detection of RNF5 mRNA and lack of confirmatory data at protein level. Microarray analysis revealed that RNF5 transcription is upregulated in carcinomas from breast, colon, esophagous, and lung. In these studies, expression of RNF5 in tumor has been confirmed at protein level on breast and melanoma tumor tissues, while no data are available on the other tumor classes (7). RNF5 mRNA has also been mentioned in patent/patent applications based on global transcription profile of prostate cancer (eg. U.S. Pat. No. 7,229,774 B2). However, no data have been reported documenting the association of RNF5 protein in prostate tumor tissues. Therefore, we disclose RNF5 as a protein without previous known association with prostate tumor and is preferably used as a marker for prostate tumor and in general for these cancer types. As described below, an antibody generated towards RNF5 protein shows a selective immunoreactivity in histological preparation of prostate cancer tissues, which indicates the presence of this protein in these cancer samples. Moreover the protein is detected on a panel of prostate tumor cell lines reinforcing the evidence.

Uncharacterized protein UNQ6126/PRO20091 (UNQ6126, LPEQ6126, synonyms: LOC100128818; Gene ID: gi|169216088; Transcript ID: GB:AY358194, Protein ID: SP:Q6UXV3); is an uncharacterized protein without previous known association with tumor and is preferably used as a marker for prostate tumor, and in general for cancers of this type. As described below, an antibody generated towards UNQ6126 protein shows a selective immunoreactivity in histological preparation of prostate cancer tissues.

Protein dpy-19 homolog 3-(DPY19L3; synonym: Dpy-19-like protein 3; Gene ID: ENSG00000178904; Transcript IDs: ENST00000319326, ENST00000392250, ENST00000342179, ENST00000392248; Protein IDs: ENSP00000315672, ENSP00000376081, ENSP00000344937, ENSP00000376079) transcript has been reported as differentially expressed in multiple myeloma (Publication Number: US20080280779A1). However no data are available at level of protein expression. In the present invention we disclose DPY19L3 protein as associated with tumor and preferably used as a marker for prostate tumor, and in general for these cancer types. As described below, an antibody generated towards DPY19L3 protein shows a selective immunoreactivity in histological preparation of prostate cancer tissues which indicates the presence of this protein in these cancer samples. Moreover the protein is detected on a panel of prostate tumor cell lines reinforcing the evidence. Finally the protein was detected on the surface of tumor cell lines by the specific antibody, suggesting that it can be exploited as target for affinity ligands with therapeutic activity.

Solute carrier family 39 member 10 (SLC39A10, synonyms: Zinc transporter ZIP10 Precursor, Zrt- and Irt-like protein 10, ZIP-10, Solute carrier family 39 member 10; gene ID: ENSG00000196950; transcript IDs: ENST00000359634, ENST00000409086; protein ID: ENSP00000352655, ENSP00000386766). belongs to a subfamily of proteins that show structural characteristics of zinc transporters. It is an integral membrane protein likely involved in zinc transport. While other members of the zinc transport family have been at least partially studied in tumors, little is known about the association of SLC39A10 with this disease. SLC39A10 mRNA has been shown to increase moderately in breast cancer tissues as compared to normal samples (approximately 1.5 fold). Loss of SLC39A10 transcription in breast cell lines has been shown to reduce the cell migratory activity in vitro (8). However, published studies on the expression of SLC39A10 in breast tumor cells are limited to the analysis of SLC39A10 transcript whilst, to the best of our knowledge, no data have been reported documenting the presence of SLC39A10 protein in these tumor cells.

SLC39A10 is mentioned in a patent application reporting long lists of differentially transcribed genes in tumor cells by using genome-scale transcription profile analysis (e.g. in Publication Number: US20070237770A1). However, studies based on transcription profile do not provide solid information regarding the expression of protein markers. The lack of correlation between mRNA and protein expression has been specifically demonstrated for LIV-1, another member of the zinc transporter family, suggesting that a similar phenomenon could be extended to other proteins of this class (9). Moreover no evidence exists on the association of SLC39A10 protein with other tumors, such as with prostate tumor classes.

In the present invention we disclose SLC39A10 as a protein without previous known association with prostate tumor classes and preferably used as a marker for prostate tumors and in general for cancers of these types. As described below, an antibody generated towards the SLC39A10 protein shows a selective immunoreactivity in histological preparation of prostate cancer tissues which indicates the presence of SLC39A10 in these cancer samples and makes SLC39A10 protein and its antibody highly interesting tools for specifically distinguishing these cancer types from a normal state.

By localization analysis of cell lines transfected with a SLC39A10 encoding plasmid we show that the protein is exposed on the cell surface and accessible to the binding of specific antibodies. This piece of data indicates that the protein is a target for anticancer therapy being accessible to the action of affinity ligands.

A further aspect of this invention is a method of screening a prostate tissue sample for malignancy, which comprises determining the presence in said sample of at least one of the above-mentioned tumor markers. This method includes detecting either the marker protein, e.g. by means of labeled monoclonal or polyclonal antibodies that specifically bind to the target protein, or the respective mRNA, e.g. by means of polymerase chain reaction techniques such as RT-PCR. The methods for detecting proteins in a tissue sample are known to one skilled in the art and include immunoradiometric, immunoenzymatic or immunohistochemical techniques, such as radioimmunoassays, immunofluorescent assays or enzyme-linked immunoassays. Other known protein analysis techniques, such as polyacrylamide gel electrophoresis (PAGE), Western blot or Dot blot are suitable as well. Preferably, the detection of the protein marker is carried out with the immune-histochemistry technology, particularly by means of High Through-Put methods that allow the analyses of the antibody immune-reactivity simultaneously on different tissue samples immobilized on a microscope slide. Briefly, each Tissue Micro Array (TMA) slide includes tissue samples suspected of malignancy taken from different patients, and an equal number of normal tissue samples from the same patients as controls. The direct comparison of samples by qualitative or quantitative measurement, e.g. by enzimatic or colorimetric reactions, allows the identification of tumors.

In one embodiment, the invention provides a method of screening a sample of prostate tissue for malignancy, which comprises determining the presence in said sample of the DPY19L3, VSTM1, RNF5, UNQ6126, or SLC39A10 protein tumor marker, alone or in combination, variants or isoforms thereof as described above.

A further aspect of the invention is a method in vitro for determining the presence of a prostate tumor in a subject, which comprises the steps of:
providing a sample of the tissue suspected of containing tumor cells;
determining the presence of a tumor marker as above defined, or a combination thereof in said tissue sample by detecting the expression of the marker protein or the presence of the respective mRNA transcript;
wherein the detection of one or more tumor markers in the tissue sample is indicative of the presence of tumor in said subject.

The methods and techniques for carrying out the assay are known to one skilled in the art and are preferably based on immunoreactions for detecting proteins and on PCR methods for the detection of mRNAs. The same methods for detecting proteins or mRNAs from a tissue sample as disclosed above can be applied.

A further aspect of this invention is the use of the tumor markers herein provided as targets for the identification of candidate antitumor agents. Accordingly, the invention provides a method for screening a test compound which comprises contacting the cells expressing a tumor-associated protein selected from: Dpy-19-like 3 (DPY19L3); V-set and transmembrane domain containing 1 (VSTM1); Ring Finger protein 5 (RNF5); Uncharacterized protein UNQ6126/PRO20091 (UNQ6126); solute carrier family 39 member 10 (SLC39A10) (zinc transporter),
with the test compound, and determining the binding of said compound to said cells. In addition, the ability of the test compound to modulate the activity of each target molecule can be assayed.

A further aspect of the invention is an antibody or a fragment thereof, which is able to specifically recognize and bind to one of the tumor-associated proteins described above. The term "antibody" as used herein refers to all types of immunoglobulins, including IgG, IgM, IgA, IgD and IgE. Such antibodies may include polyclonal, monoclonal, chimeric, single chain, antibodies or fragments such as Fab or scFv. The antibodies may be of various origin, including human, mouse, rat, rabbit and horse, or chimeric antibodies. The production of antibodies is well known in the art. For the production of antibodies in experimental animals, various hosts including goats, rabbits, rats, mice, and others, may be immunized by injection with polypeptides of the present invention or any fragment or oligopeptide or derivative thereof which has immunogenic properties or forms a suitable epitope. Monoclonal antibodies may be produced following the procedures described in Kohler and Milstein, Nature 265:495 (1975) or other techniques known in the art.

The antibodies to the tumor markers of the invention can be used to detect the presence of the marker in histologic preparations or to distinguish tumor cells from normal cells. To that purpose, the antibodies may be labeled with radioactive, fluorescent or enzyme labels.

In addition, the antibodies can be used for treating proliferative diseases by modulating, e.g. inhibiting or abolishing the activity of a target protein according to the invention. Therefore, in a further aspect the invention provides the use of antibodies to a tumor-associated protein selected from: DPY-19-like 3 (DPY19L3); V-set and transmembrane domain containing 1 (VSTM1); Ring Finger protein 5 (RNF5); Uncharacterized protein UNQ6126/PRO20091 (UNQ6126); solute carrier family 39 member 10 (SLC39A10) (zinc transporter), for the preparation of a therapeutic agent for the treatment of proliferative diseases. For use in therapy, the antibodies can be formulated with suitable carriers and excipients, optionally with the addition of adjuvants to enhance their effects.

A further aspect of the invention relates to a diagnostic kit containing suitable means for detection, in particular the polypeptides or polynucleotides, antibodies or fragments or derivatives thereof described above, reagents, buffers, solutions and materials needed for setting up and carrying out the immunoassays, nucleic acid hybridization or PCR assays described above. Parts of the kit of the invention can be packaged individually in vials or bottles or in combination in containers or multicontainer units.

Left panel: Comassie staining of purified His-tag DPY19L3 fusion protein separated by SDS-PAGE; Right panel: WB on the recombinant DPY19L3 protein stained with anti-DPY19L3 antibody. Arrow marks the protein band of the expected size. Molecular weight markers are reported on the left.

Figure 1:
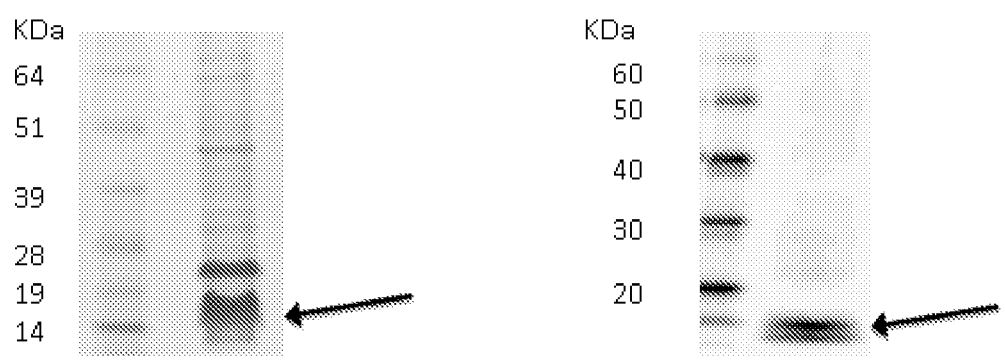
FIG. 1. Analysis of purified DPY19L3 recombinant protein
Figure 2:
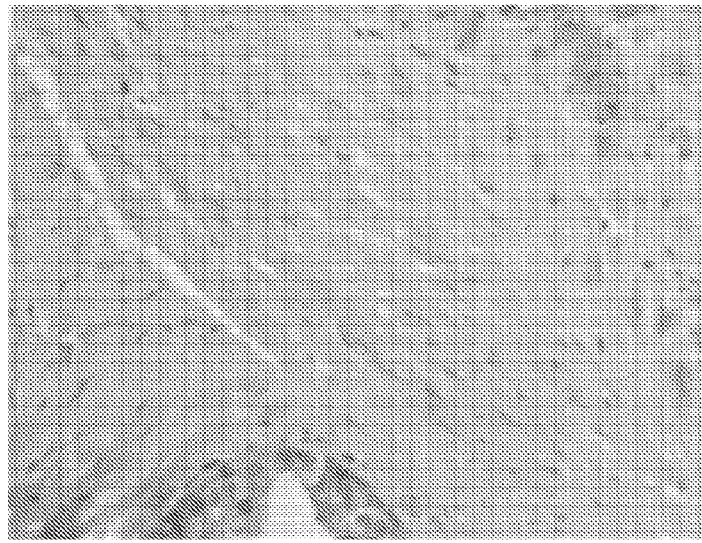
Figure 2:
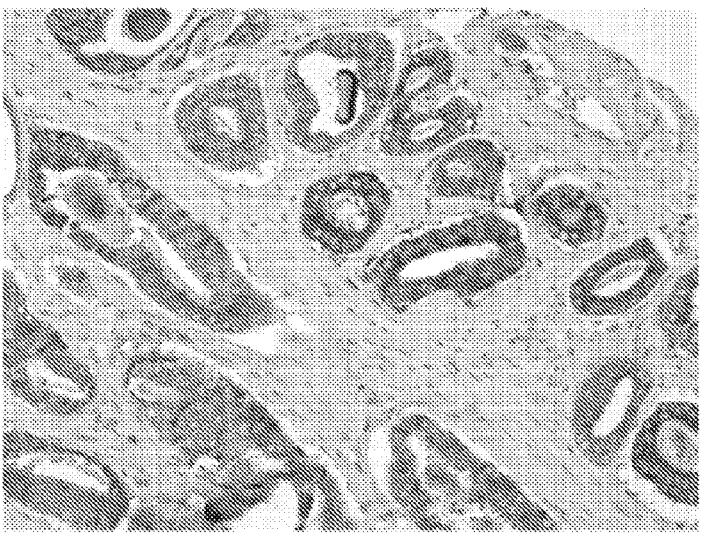

FIG. 2. Staining of prostate tumor TMA with anti-DPY19L3 antibodies

Examples of TMA of tumor (lower panel) and normal tissue samples (upper panel) stained with anti-DPY19L3 antibodies. The antibody-stains specifically tumor cells (in dark gray).

Figure 3:
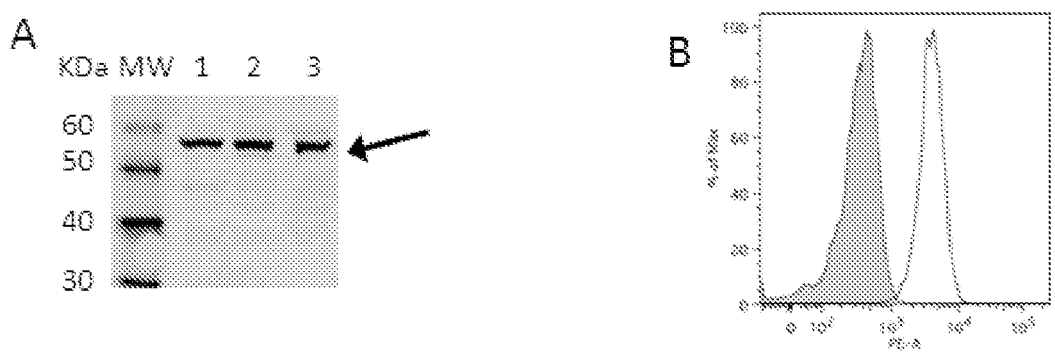

FIG. 3. Expression and localization of DPY19L3 in tumor cell lines

Left panel: Western blot analysis of DPY19L3 expression in total protein extracts separated by SDS-PAGE from DU145 (1), PC3 (2); LN-CAP (3) prostate derived tumor cells. Arrow marks the protein band of the expected size. Molecular weight markers are reported on the left.

Right panel: Flow cytometry analysis of DPY19L3 cell surface localization in MOLT-4 tumor cells stained with a control antibody (filled curve or with anti-DPY19L3 antibody (empty curve). X axis, Fluorescence scale; Y axis, Cells (expressed as % relatively to major peaks).

Figure 4:
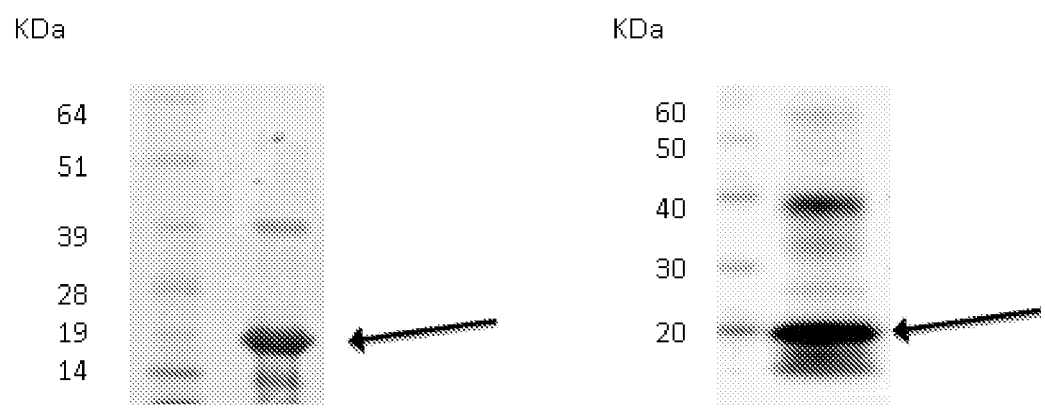

FIG. 4. Analysis of purified VSTM1 recombinant protein

Left panel: Comassie staining of purified His-tag VSTM1 fusion protein separated by SDS-PAGE; Right panel: WB on the recombinant protein stained with anti-VSTM1 antibody. Arrow marks the protein band of the expected size. The high molecular weight bands correspond to multimer forms of VSTM1 protein. Molecular weight markers are reported on the left.

Figure 5:
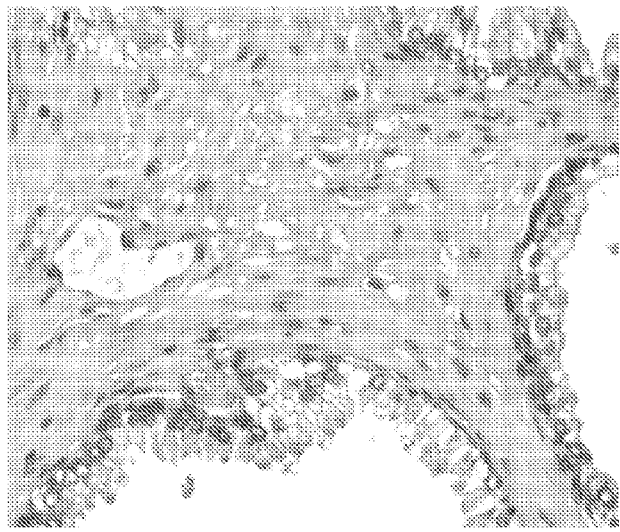
Figure 5:
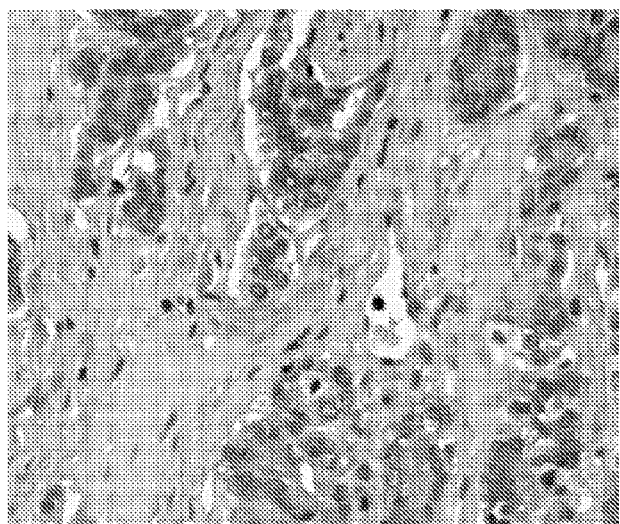

FIG. 5. Staining of prostate tumor TMA with anti-VSTM1 antibodies

Examples of TMA of tumor (lower panel) and normal tissue samples (upper panel) stained with anti-VSTM1 antibodies. The antibody-stains specifically tumor cells (in dark gray).

Figure 6:
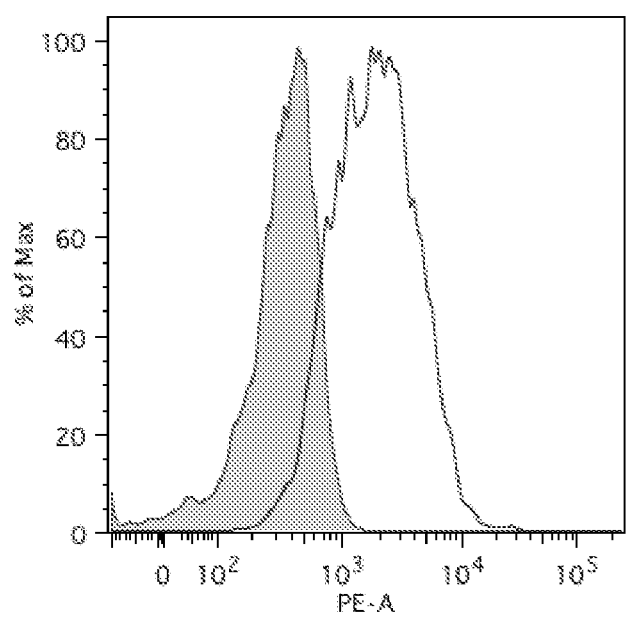

FIG. 6. Expression and localization of VSTM1 in tumor cell lines

Flow cytometry analysis of VSTM1 cell surface localization in MOLT-4 tumor cells stained with a control antibody (filled curve) or with anti-VSTM1 antibody (empty curve). X axis, Fluorescence scale; Y axis, Cells (expressed as % relatively to major peaks).

Figure 7:
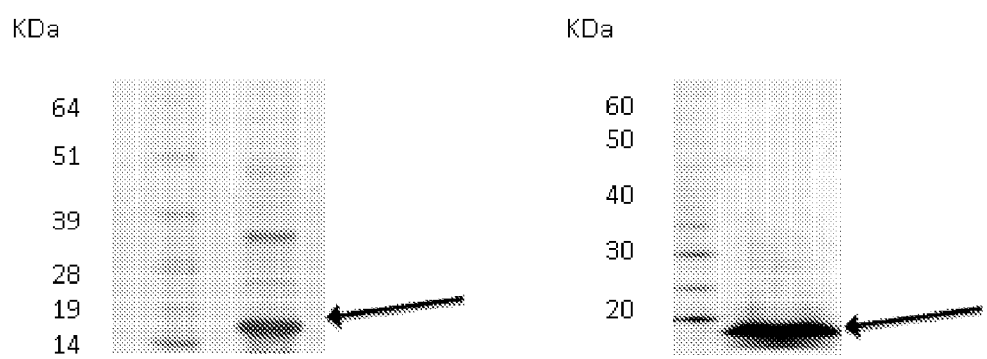

FIG. 7. Analysis of purified RNF5 recombinant protein

Left panel: Comassie staining of purified His-tag RNF5 fusion protein separated by SDS-PAGE; Right panel: WB on the recombinant protein stained with anti-RNF5 antibody. Arrow marks the protein band of the expected size. Molecular weight markers are reported on the left.

Figure 8:
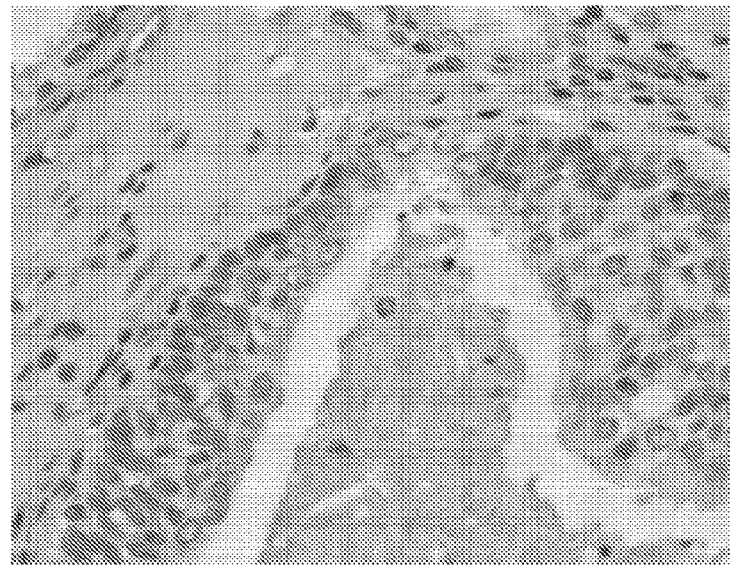
Figure 8:
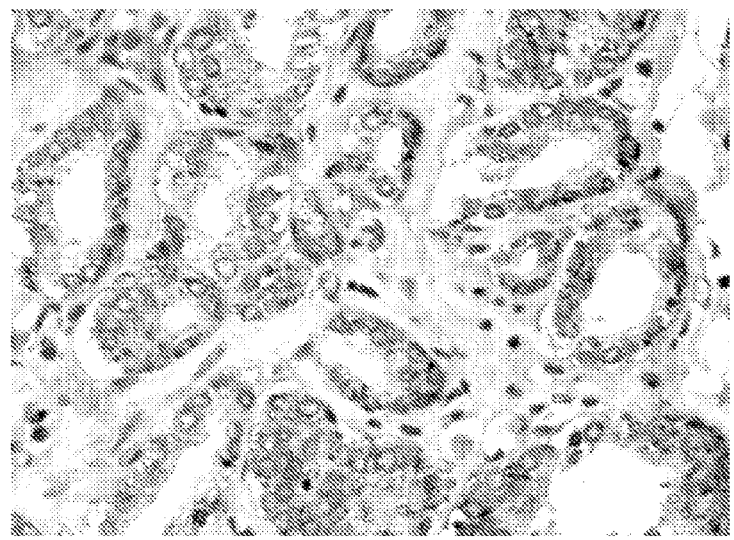

FIG. 8. Staining of prostate tumor TMA with anti-RNF5 antibodies

Examples of TMA of tumor (lower panel) and normal tissue samples (upper panel) stained with anti-RNF5 antibodies. The antibody-stains specifically tumor cells (in dark gray).

Figure 9:
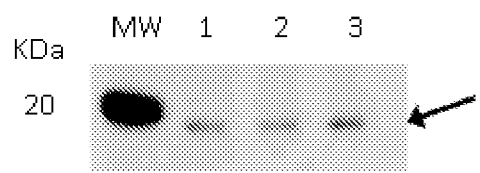

FIG. 9. Expression of RNF5 in prostate tumor cell lines

Western blot analysis of RNF5 expression in total protein extracts separated by SDS-PAGE from DU145 (1) PC3 (2); LN-CAP (3) prostate derived tumor cells. Arrow marks the protein band of the expected size. Molecular weight markers are reported on the left.

Figure 10:
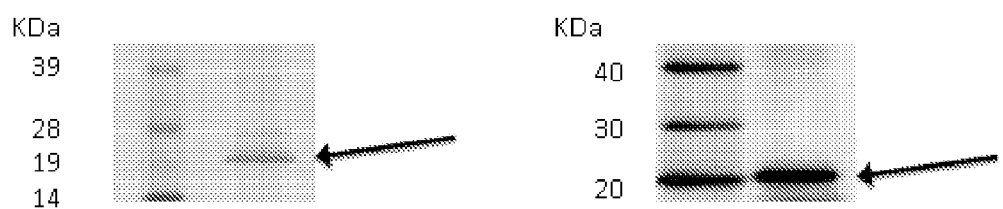

FIG. 10. Analysis of purified UNQ6126 recombinant protein

Left panel: Comassie staining of purified His-tag UNQ6126 fusion protein separated by SDS-PAGE; Right panel: WB on the recombinant UNQ6126 protein stained with anti-UNQ6126 antibody. Arrow marks the protein band of the expected size. Molecular weight markers are reported on the left.

Figure 11:
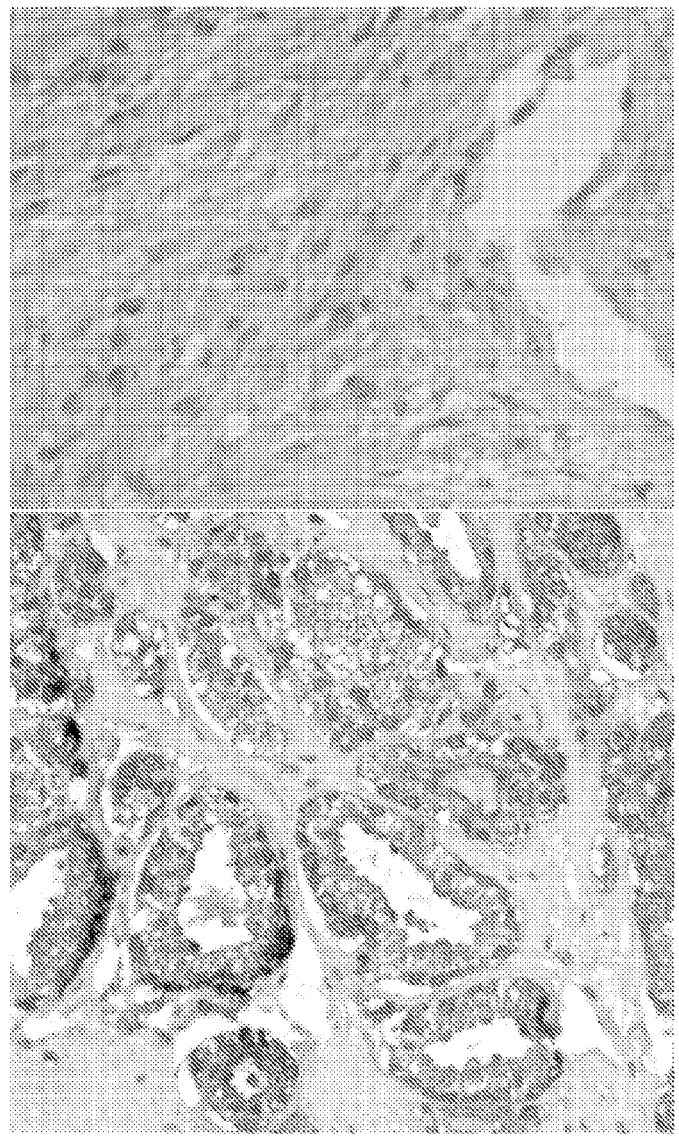

FIG. 11. Staining of prostate tumor TMA with anti-UNQ6126 antibodies

Examples of TMA of tumor (lower panel) and normal tissue samples (upper panel) stained with anti-UNQ6126 antibodies. The antibodies stain specifically tumor cells (in dark gray).

Figure 12:
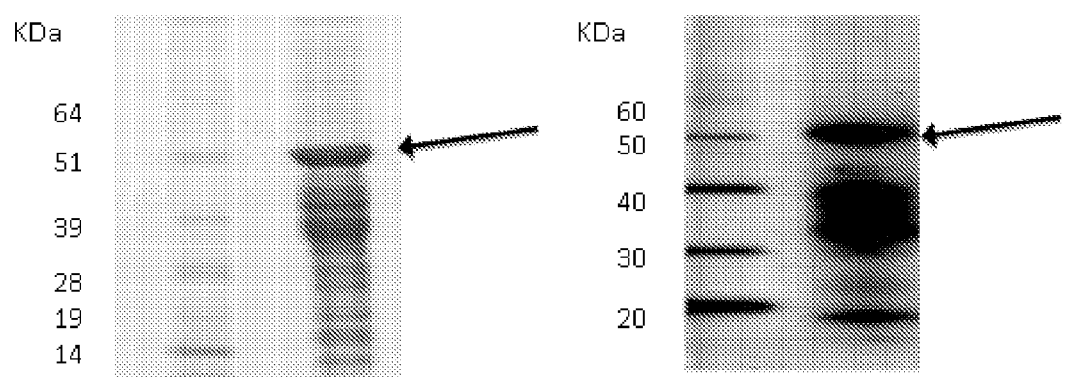

FIG. 12. Analysis of purified SLC39A10 recombinant protein

Left panel: Comassie staining of purified His-tag MEGF8 fusion protein expressed in *E. coli* separated by SDS-PAGE; Right panel: WB on the purified recombinant SLC39A10 protein stained with anti-SLC39A10 antibody. Arrow marks the protein band of the expected size. The low molecular weight bands correspond to partially degraded forms of SLC39A10 protein. Molecular weight markers are reported on the left.

Figure 13:
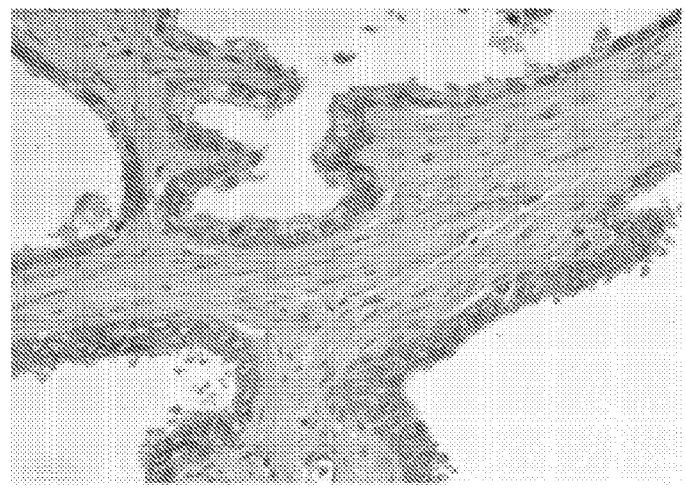
Figure 13:
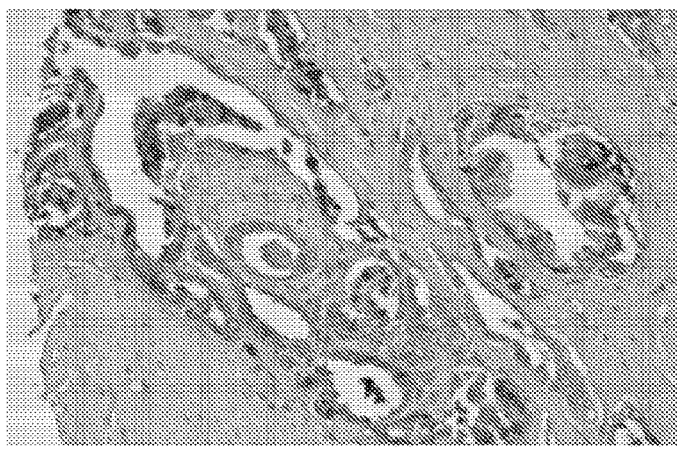

FIG. 13. Staining of prostate tumor TMA with anti-SLC39A10 antibodies

Examples of TMA of tumor (lower panel) and normal tissue samples (upper panel) stained with anti-SLC39A10 antibodies. The antibodies stain specifically tumor cells (in dark gray).

Figure 14:
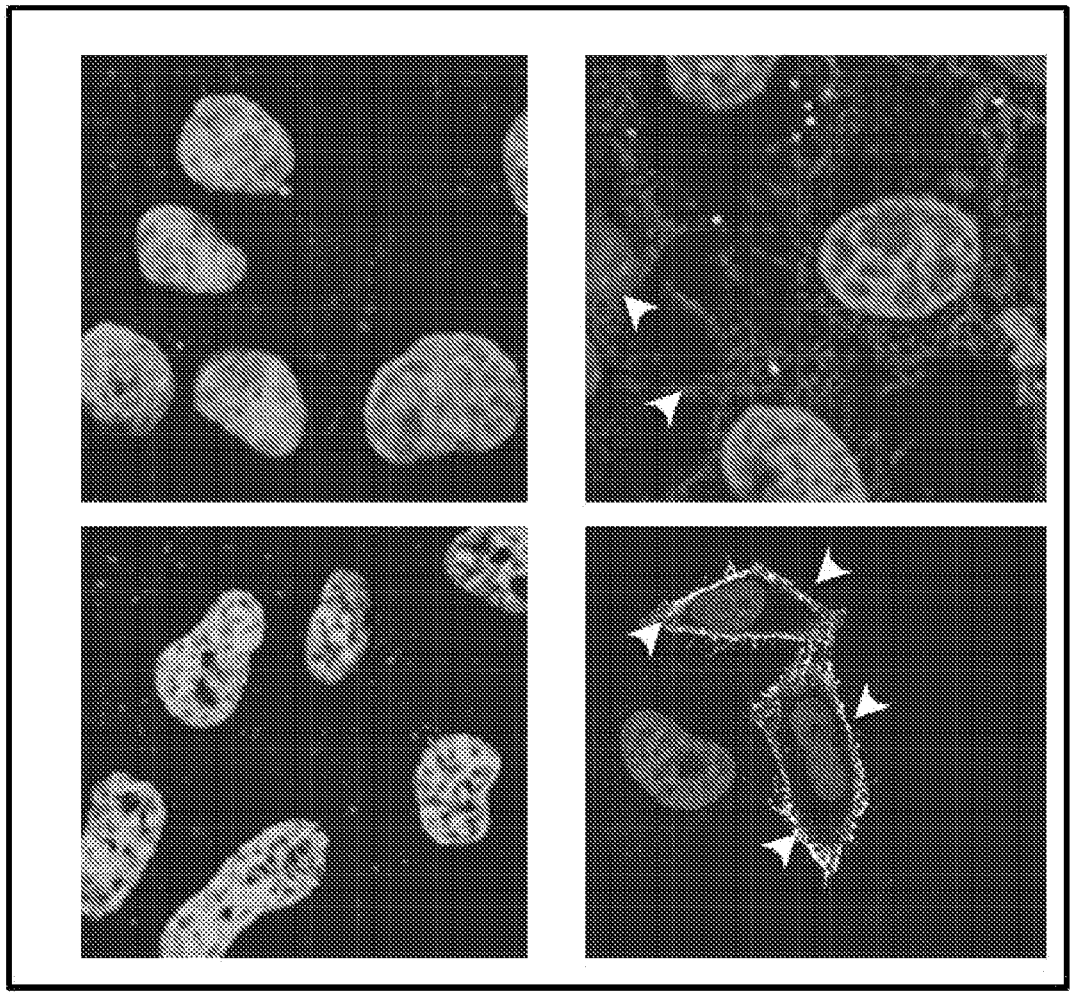

FIG. 14. Confocal microscopy analysis of expression and localization of SLC39A10 in transfected cells HeLa cells transfected with the empty pcDNA3 vector (upper panels) or with the plasmid construct encoding the SLC39A10 gene (lower panels) stained with secondary antibodies (left panels) and with anti-SLC39A10 antibodies (right panels). Arrowheads mark surface specific localization.

The following examples further illustrate the invention.

EXAMPLES

Example 1

Generation of Recombinant Human Protein Antigens and Antibodies to Identify Tumor Markers Methods The entire coding region or suitable fragments of the genes encoding the target proteins, were designed for cloning and expression using bioinformatic tools with the human genome sequence as template (Lindskog M et al (2005)). Where present, the leader sequence for secretion was replaced with the ATG codon to drive the expression of the recombinant proteins in the cytoplasm of *E.coli*. For cloning, genes were PCR-amplified from clones derived from the Mammalian Gene Collection (mgc.nci.nih.gov/) or from cDNA mixtures generated from pools of total RNA derived from Human testis, Human placenta, Human bone marrow, Human fetal brain, using specific primers. Clonings were designed so as to fuse a 10 histidine tag sequence at the 5' end, annealed to in house developed vectors, derivatives of vector pSP73 (Promega) adapted for the T4 ligation independent cloning method (Nucleic Acids Res. 1990 Oct. 25; 18(20): 6069-6074) and used to transform E.coli NovaBlue cells recipient strain. E.coli transformants were plated onto selective LB plates containing 100 g/ml ampicillin (LB Amp) and positive. E.coli clones were identified by restriction enzyme analysis of purified plasmid followed by DNA sequence analysis. For expression, plasmids were used to transform BL21-(DE3) E.coli cells and BL21-(DE3) E.coli cells harboring the plasmid were inoculated in ZYP-5052 growth medium (Studier, 2005) and grown at 37° C. for 24 hours. Afterwards, bacteria were collected by centrifugation, lysed into B-Per Reagent containing 1 mM MgC12, 100 units DNAse I (Sigma), and 1mg/ml lysozyme (Sigma). After 30 min at room temperature under gentle shaking, the lysate was clarified by centrifugation at 30.000g for 40 min at 4° C. All proteins were purified from the inclusion bodies by resuspending the pellet coming from lysate centrifugation in 40 mM TRIS-HC1, 1 mM TCEP {Tris(2-carboxyethyl)-phosphine hydrochloride, Pierce} and 6M guanidine hydrochloride, pH 8 and performing an IMAC in denaturing conditions. Briefly, the resuspended material was clarified by centrifugation at 30.000 g for 30 min and the supernatant was loaded on 0.5 ml columns of Ni-activated Chelating Sepharose Fast Flow (Pharmacia). The column was washed with 50 mM TRIS-HC1 buffer, 1 mM TCEP, 6M urea, 60 mM imidazole, 0.5M NaC1, pH 8. Recombinant proteins were eluted with the same buffer containing 500 mM imidazole. Proteins were analyzed by SDS-Page and their concentration was determined by Bradford assay using the BIORAD reagent (BIORAD) with a bovine serum albumin standard according to the manufacturer's recommendations.

To generate antisera, the purified proteins were used to immunize CD1 mice (6 week-old females, Charles River laboratories, 5 mice per group) intraperitoneally, with 3 protein doses of 20 micrograms each, at 2 week-interval. Freund's complete adjuvant was used for the first immunization, while Freund's incomplete adjuvant was used for the two booster doses. Two weeks after the last immunization animals were bled and sera collected from each animal was pooled.

Results

Gene fragments of the expected size were obtained by PCR from specific clones of the Mammalian Gene Collection or, alternatively, from cDNA generated from pools of total RNA derived from Human testis, Human placenta, Human bone marrow, Human fetal brain, using primers specific for each gene.

For the DPY19L3 gene, a fragment corresponding to nucleotides 158 to 463 of the transcript ENST00000392250 and encoding a protein of 102 residues, corresponding to the amino acid region from 1 to 102 of ENSP00000376081 sequence was obtained.

For the VSTM1 gene, a fragment corresponding to nucleotides 225 to 578 of the transcript ENST00000338372 and encoding a protein of 118 residues, corresponding to the amino acid region from 17 to 134 of ENSP00000343366 sequence was obtained.

For the RNF5 gene, a fragment corresponding to nucleotides 159 to 509 of the transcript ENST00000383289 and encoding a protein of 101 residues, corresponding to the amino acid region from 1 to 117 of ENSP00000372776 sequence was obtained.

For the UNQ6126 gene, a fragment corresponding to a fragment corresponding to nucleotides 88 to 471 of the transcript gi|169216088|ref|XM_001719570.1| and encoding a protein of 128 residues, and encoding an amino acid region from 30 to 147 of sp|Q6UXV3|YV010 sequence was obtained.

For the SLC39A10 gene, a DNA fragment corresponding to nucleotides 154-1287 of the transcript ENST00000359634 and encoding a protein of 378 residues, corresponding to the amino acid region from 26 to 403 of ENSP00000352656 sequence was obtained.

A clone encoding the correct amino acid sequence was identified for each gene/gene fragment and, upon expression in E. coli, a protein of the correct size was produced and subsequently purified using affinity chromatography (FIGS. 1, 4, 7, 10, 12, left panels). As shown in the figures, in some case SDS-PAGE analysis of affinity-purified recombinant proteins revealed the presence of extra bands, of either higher and/or lower masses. Mass spectrometry analysis confirmed that they corresponded to either aggregates or degradation products of the protein under analysis. Antibodies generated by immunization specifically recognized their target proteins in Western blot (WB) (FIGS. 1, 4, 7, 10, 12, right panels).

Example 2

Tissue Profiling by Immune-Histochemistry

Methods

The analysis of the antibodies' capability to recognize their target proteins in tumor samples was carried out by Tissue Micro Array (TMA), a miniaturized immuno-histochemistry technology suitable for HTP analysis that allows to analyse the antibody immuno-reactivity simultaneously on different tissue samples immobilized on a microscope slide. Since the TMAs include both tumor and healthy tissues, the specificity of the antibodies for the tumors can be immediately appreciated. The use of this technology, differently from approaches based on transcription profile, has the important advantage of giving a first-hand evaluation on the potential of the markers in clinics. Conversely, since mRNA levels not always correlate with protein levels, studies based on transcription profile do not provide solid information regarding the expression of protein markers.

A tissue microarray was prepared containing formalin-fixed paraffin-embedded cores of human tissues from patients affected by prostate cancer and corresponding normal tissues as controls and analyzed using the specific antibody sample. A TMA design consisted in 10 prostate tumor samples and 10 normal tissues from 5 well pedigreed patients (equal to two tumor samples and 2 normal tissues from each patient) to identify promising target molecules differentially expressed in cancer and normal tissues. The direct comparison between tumor and normal tissues of each patient allowed the identification of antibodies that stain specifically tumor cells and provided indication of target expression in prostate tumor. To confirm the association of each protein with prostate tumors a second tissue microarray was used containing 100 formalin-fixed paraffin-embedded cores of human prostate tissues from 50 patients (equal to two tissue samples from each patient).

All formalin fixed, paraffin embedded tissues used as donor blocks for TMA production were selected from the archives at the IEO (Istituto Europeo Oncologico, Milan). Corresponding whole tissue sections were examined to confirm diagnosis and tumor classification, and to select representative areas in donor blocks. Normal tissues were defined as microscopically normal (non-neoplastic) and were generally selected from specimens collected from the vicinity of surgically removed tumors. The TMA production was performed essentially as previously described (Kononen J et al. (1998) Nature Med. 4:844-847; Kallioniemi O P et al. (2001) Hum. Mol. Genet. 10:657-662). Briefly, a hole was made in the recipient TMA block. A cylindrical core tissue sample (1 mm in diameter) from the donor block was acquired and deposited in the recipient TMA block. This was repeated in an automated tissue arrayer "Galileo TMA CK 3500" (BioRep, Milan) until a complete TMA design was produced. TMA recipient blocks were baked at 42 <0>C for 2 h prior to sectioning. The TMA blocks were sectioned with 2-3 mm thickness using a waterfall microtome (Leica), and placed onto poli-L-lysinated glass slides for immunohistochemical analysis. Automated immunohistochemistry was performed as previously described (Kampf C. et al (2004) Clin. Proteomics 1:285-300). In brief, the glass slides were incubated for 30' min in 60° C., de-paraffinized in xylene (2×15 min) using the Bio-Clear solution (Midway.

Scientific, Melbourne, Australia), and re-hydrated in graded alcohols. For antigen retrieval, slides were immersed 0.01 M Na-citrate buffer, pH 6.0 at 99° C. for 30 min Slides were placed in the Autostainer (R) (DakoCytomation) and endogenous peroxidase was initially blocked with 3% $H_2O_2$, for 5 min. Slides were then blocked in Dako Cytomation Wash Buffer containing 5% Bovine serum albumin (BSA) and subsequently incubated with mouse antibodies for 30' (dilution 1:200 in Dako Real™ dilution buffer). After washing with DakoCytomation wash buffer, slides were incubated with the goat anti-mouse peroxidase conjugated Envision(R) for 30 min each at room temperature (DakoCytomation). Finally, diaminobenzidine (DakoCytomation) was used as chromogen and Harris hematoxylin (Sigma-Aldrich) was used for counterstaining. The slides were mounted with Pertex(R) (Histolab).

The staining results have been evaluated by a trained pathologist at the light microscope, and scored according to both the percentage of immunostained cells and the intensity of staining. The individual values and the combined score (from 0 to 300) were recorded in a custom-tailored database. Digital images of the immunocytochemical findings have been taken at a Leica DM LB light microscope, equipped with a Leica DFC289 color camera.

Results

TMAs design were obtained, representing tumor tissue samples and normal tissues, derived from patients affected by prostate tumor. The results from tissue profiling showed that the antibodies specific for the recombinant proteins (see Example 1) are strongly immunoreactive prostate tumor cancer tissues, while no or poor reactivity was detected in normal tissues, indicating the presence of the target proteins in prostate tumors. Based on this finding, the detection of target proteins in tissue samples can be associated with prostate tumor.

The capability of target-specific antibodies to stain prostate tumor tissues is summarized in Table I. Representative examples of microscopic enlargements of tissue samples stained by each antibody are reported in FIGS. 2; 5; 8; 11; 13).

Table I reports the percentage of positive prostate tumor samples after staining with the target specific antibodies

TABLE I

| Marker name | Percentage of positive prostate tumor samples |
|---|---|
| DPY19L3 | 81 |
| VSTM1 | 80 |

TABLE I-continued

| Marker name | Percentage of positive prostate tumor samples |
|---|---|
| RNF5 | 60 |
| SLC39A10 | 20 |

Example 3

Expression and Cell Localization of Target Protein in Transfected Mammalian Cells Methods The specificity of the antibodies for each target protein was assessed by western blot and/or confocal microscopy analysis of eukaryotic cells transiently transfected with a plasmid construct containing the complete sequence of the gene encoding the target proteins. An example of this type of confocal microscopy experiments is represented for SLC39A10 (corresponding to Transcript ID ENST00000359634).

To this aim, cDNA were generated from pools of total RNA derived from Human testis, Human placenta, Human bone marrow, Human fetal brain, in reverse transcription reactions and the entire coding regions were PCR-amplified with specific primers pairs. PCR products were cloned into plasmid pcDNA3 (Invitrogen). HeLa cells were grown in DMEM-10% FCS supplemented with 1 mM Glutamine were transiently transfected with preparation of the resulting plasmid and with the empty vector as negative control using the Lipofectamine-2000 transfection reagent (Invitrogen). After 48 hours, cells were collected, lysed with PBS buffer containing 1% Triton X100 and expression of target proteins was assessed by Western blot analysis on total cell extracts (corresponding to $2 \times 10^5$ cells) using specific antibodies. Western blot was performed by separation of the protein extracts on pre-cast SDS-PAGE gradient gels (NuPage 4-12% Bis-Tris gel, Invitrogen) under reducing conditions, followed by electro-transfer to nitrocellulose membranes (Invitrogen) according to the manufacturer's recommendations. The membranes were blocked in blocking buffer composed of 1×PBS-0.1% Tween 20 (PBST) added with 10% dry milk, for 1 h at room temperature, incubated with the antibody diluted 1:2500 in blocking buffer containing 1% dry milk and washed in PBST-1%. The secondary HRP-conjugated antibody (goat anti-mouse immunoglobulin/HRP, Perkin Elmer) was diluted 1:5000 in blocking buffer and chemiluminescence detection was carried out using a Chemidoc-IT UVP CCD camera (UVP) and the Western lightning™ cheminulescence Reagent Plus (Perkin Elmer), according to the manufacturer's protocol. Surface localization of target protein SLC39A10 was assessed by cell surface staining and confocal microscopy analysis in HeLa transfected cells. HeLa cells were transfected with the SLC39A10 construct or with the empty vector ($2 \times 10^4$ per well). The cells were plated on glass cover slips and after 48 h were washed with PBS and fixed with 3% p-formaldheyde solution in PBS for 20 min at RT. For surface staining, cells were incubated overnight at 4° C. with polyclonal antibodies (1:200). The cells were then stained with Alexafluor 488-labeled goat anti-mouse antibodies (Molecular Probes). DAPI (Molecular Probes) was used to visualize nuclei; Live/Dead® red fixable (Molecular Probes) was used to visualize membrane. The cells were mounted with glycerol plastine and observed under a laser-scanning confocal microscope (LeicaSPS).

Results

Analysis of expression and localization of SLC39A10 was carried by confocal microscopy analysis of HeLa cells transiently transfected with a marker encoding plasmid. As shown in FIG. 14, anti-SLC39A10 antibodies were capable of binding specifically the surface of Hela cells transfected with the SLC39A10 encoding plasmid, while no binding was observed on cells transfected with the empty pcDNA3 vector. This indicates that the target protein is localized on the extracellular plasma membrane, accessible to the external environment. This finding reinforces the relevance of identified target protein for future development of both diagnostic and therapeutic tools, such as monoclonal antibodies.

Example 4

Expression and Surface Localization of Target Proteins in Tumor Cell Lines

Expression and localization of target proteins was assessed by immunoblot and flow cytometry analysis of the prostate tumor cell lines DU145, PC3 and LN-CAP. For immunoblot analysis, cells were grown under manufacturer's recommended medium, lysed and subjected to immunoblot as described in the previous examples. For flow cytometry analysis of marker surface exposure, cells ($2\times10^4$ per well) were pelleted in 96 U-bottom microplates by centrifugation at 200×g for 5 min at 4° C. and incubated for 1 hour at 4° C. with the appropriate dilutions of the marker-specific antibodies. The cells were washed twice in PBS-5% FCS and incubated for 20 min with the appropriate dilution of R-Phycoerythrin (PE)-conjugated secondary antibodies (Jackson Immuno Research, PA, USA) at 4° C. After washing, cells were analysed by a FACS Canto II flow cytometer (Becton Dickinson). Data were analyzed with FlowJo 8.3.3 program.

Results

Expression of target proteins was carried out on total extracts of prostate tumor cell lines by immunoblot. Examples of the results are provided for DPY19L3 and RNF5 showing that protein bands of expected size were detected by the marker-specific antibodies (FIG. 3A and FIG. 9). Localization analysis was performed by surface staining and flow cytometry analysis of tumor cell lines. Results are shown for DPY19L3 and VSTM1 in FIG. 3B and FIG. 6 showing that DPY19L3- and VSTM1-specific antibodies were capable of binding specifically the surface of tumor cell lines. This indicates that these target proteins are localized on the extracellular plasma membrane, are accessible to the external environment and, therefore, could be exploited as therapeutic targets.

REFERENCES

1) Anderson, L., and Seilhamer, J. (1997). A comparison of selected mRNA and protein abundances in human liver. Electrophoresis 18, 533-537;
2) Chen, G., Gharib, T. G., Wang, H., Huang, C. C., Kuick, R., Thomas, D. G., Shedden, K. A., Misek, D. E., Taylor, J. M., Giordano, T. J., Kardia, S. L., Iannettoni, M. D., Yee, J., Hogg, P. J., Orringer, M. B., Hanash, S. M., and Beer, D. G. (2003) Protein profiles associated with survival in lung adenocarcinoma. Proc. Natl. Acad. Sci. U.S.A 100, 13537-13542;
3) Ginestier, C., Charafe-Jauffret, E., Bertucci, F., Eisinger, F., Geneix, J., Bechlian, D., Conte, N., Adelaide, J., Toiron, Y., Nguyen, C., Viens, P., Mozziconacci, M. J., Houlgatte, R., Birnbaum, D., and Jacquemier, J. (2002) Distinct and complementary information provided by use of tissue and DNA microarrays in the study of breast tumor markers. Am. J. Pathol. 161, 1223-1233;
4) Gygi, S. P., Rochon, Y., Franza, B. R., and Aebersold, R. (1999) Correlation between protein and mRNA abundance in yeast. Mol. Cell. Biol. 19, 1720-1730; Nishizuka, S., Charboneau, L., Young, L., Major, S., Reinhold, W. C., Waltham, M., Kouros-Mehr, H., Bussey, K. J., Lee, J. K., Espina, V., Munson, P. J., Petricoin, E., III, Liotta, L. A., and Weinstein, J. N. (2003) Proteomic profiling of the NCl-60 cancer cell lines using new high-density reverse-phase lysate microarrays. Proc. Natl. Acad. Sci. U.S.A 100, 14229-14234;
5) Tyers, M., and Mann, M. (2003) From genomics to proteomics. Nature 422, 193-197;
6) Didier, C., Broday, L., Bhoumik, A., Israeli, S., Takahashi, S., Nakayama, K., Thomas, S. M., Turner, C. E., Henderson, S., Sabe, H. and Ronai, Z. (2003) RNF5, a RING finger protein that regulates cell motility by targeting paxillin ubiquitination and altered localization Mol. Cell. Biol. 23: 5331-5345.
7) Bromberg, K. D., Kluger, H. M., Delaunay, A., Abbas, S., DiVito, K. A., Krajewski, S, and Ronai, Z. (2007) Increased expression of the E3 ubiquitin ligase RNF5 is associated with decreased survival in breast cancer Cancer Res. 67, 8172-8179.
8) Kagara N, Tanaka N, Noguchi S, Hirano T. (2007) Zinc and its transporter ZIP10 are involved in invasive behavior of breast cancer cells. Cancer Sci. 98:692-697.
9) Kasper G, Weiser A A, Rump A, Sparbier K, Dahl E, Hartmann A, Wild P, Schwidetzky U, Castaños-Vélez E, Lehmann K. (2005) Expression levels of the putative zinc transporter LIV-1 are associated with a better outcome of breast cancer patients. Int J. Cancer. 117:961-973.

The invention claimed is:

1. A method comprising:
    (a) providing a sample of a prostate tissue;
    (b) detecting whether the sample of the prostate tissue expresses at least one tumor marker selected from the group consisting of:
        i) a polypeptide comprising the amino acid sequence set forth in SEQ ID NO:11; and
        ii) a polypeptide comprising the amino acid sequence set forth in SEQ ID NO:7,
    wherein the detecting is performed by immunohistochemical analysis using an antibody that specifically binds to the at least one tumor marker;
    (c) determining that the expression of the at least one tumor marker in the sample of the prostate tissue is
        (i) higher than in a non-malignant prostate tissue control sample; or
        (ii) same or lower than in the non-malignant prostate tissue control sample,
    (d) identifying the sample of the prostate tissue expressing the at least one tumor marker at a higher level than in the non-malignant prostate tissue control sample as having a prostate malignancy, and identifying the sample of the prostate tissue expressing the at least one tumor marker at the same or lower level than in the non-malignant prostate tissue control sample as not having a prostate malignancy, and
    (e) administering to a subject from whom the sample of the prostate tissue is obtained that expresses the at least one tumor marker at a higher level than in the non-malignant prostate tissue control sample, a monoclonal antibody that specifically binds the at least one tumor marker for treating the prostate malignancy.

2. The method of claim 1, wherein the at least one tumor marker is a polypeptide comprising the amino acid sequence forth in SEQ ID NO:11.

3. The method of claim 1, wherein the sample of the prostate tissue is from a human subject.

4. The method of claim 1, wherein the sample of the prostate tissue is screened for expression of at least two different tumor markers.

5. The method of claim 1, wherein the sample of the prostate tissue is screened for expression of at least three different tumor markers.

6. The method of claim 1, wherein the sample of the prostate tissue is screened for expression of at least four different tumor markers.

7. The method of claim 1, wherein the sample of the prostate tissue is screened for expression of five different tumor markers.

8. A method for determining whether a human patient has a prostate malignancy, the method comprising:
    (a) providing a sample of a prostate tissue from the patient;
    (b) determining that the sample of the prostate tissue expresses at least one tumor marker at a higher level compared to a non-malignant prostate tissue control sample, wherein the at least one tumor marker is a polypeptide selected from the group consisting of a polypeptide comprising the amino acid sequence of SEQ ID NO: 7 and a polypeptide comprising the amino acid sequence of SEQ ID NO: 11, and wherein the detecting is performed by immunohistochemical analysis by contacting the sample of the prostate tissue with an antibody that specifically binds to the at least one tumor marker; and
    (c) diagnosing the patient from whom the sample of the prostate tissue is obtained as having a prostate malignancy.

9. The method of claim 8, wherein the antibody is a monoclonal antibody.

10. The method of claim 8, wherein the at least one tumor marker is SEQ ID NO: 11.

11. The method of claim 10, wherein the antibody is a monoclonal antibody that specifically binds to SEQ ID NO: 11.

12. The method of claim 11, wherein the monoclonal antibody binds to an epitope within SEQ ID NO: 10.

* * * * *

UNITED STATES PATENT AND TRADEMARK OFFICE
CERTIFICATE OF CORRECTION

PATENT NO.         : 8,921,058 B2
APPLICATION NO.    : 13/503396
DATED              : December 30, 2014
INVENTOR(S)        : Renata Grifantini et al.

It is certified that error appears in the above-identified patent and that said Letters Patent is hereby corrected as shown below:

In the Claims

Col. 58, line 36, Claim 2, before "forth" insert -- set --.

Signed and Sealed this
Twenty-first Day of April, 2015

Michelle K. Lee
*Director of the United States Patent and Trademark Office*